US008921420B2

(12) United States Patent
Poessel et al.

(10) Patent No.: US 8,921,420 B2
(45) Date of Patent: Dec. 30, 2014

(54) METHOD FOR PREPARING DICAFFEOYLQUINIC ACIDS AND USE THEREOF IN COMBATING APHIDS

(75) Inventors: Jean-Luc Poessel, Le Thor (FR); Marie-Hélène Collet, Saint Saturnin les Avignon (FR); Yves Noel Elie Rahbe, Villeurbanne (FR)

(73) Assignee: Institut National de la Recherche Agronomique, Paris (FR)

(*) Notice: Subject to any disclaimer, the term of this patent is extended or adjusted under 35 U.S.C. 154(b) by 950 days.

(21) Appl. No.: 12/865,658

(22) PCT Filed: Jan. 30, 2009

(86) PCT No.: PCT/FR2009/050137
§ 371 (c)(1),
(2), (4) Date: Nov. 15, 2010

(87) PCT Pub. No.: WO2009/095624
PCT Pub. Date: Aug. 6, 2009

(65) Prior Publication Data
US 2011/0054022 A1    Mar. 3, 2011

(30) Foreign Application Priority Data

Feb. 1, 2008  (FR) ..................... 08 00561

(51) Int. Cl.
| C07C 67/48 | (2006.01) |
| A01N 37/10 | (2006.01) |
| A01P 7/04 | (2006.01) |
| C07C 51/48 | (2006.01) |
| A01N 37/38 | (2006.01) |
| C07C 51/42 | (2006.01) |

(52) U.S. Cl.
CPC ............... *A01N 37/38* (2013.01); *C07C 51/48* (2013.01); *C07C 51/42* (2013.01)
USPC ........................................... 514/533; 560/55

(58) Field of Classification Search
USPC .......................................... 560/55; 514/533
See application file for complete search history.

(56) References Cited

U.S. PATENT DOCUMENTS

| 4,872,987 A | 10/1989 | Kopsch et al. |
| 5,395,624 A | 3/1995 | Li et al. |
| 7,350,331 B1 | 4/2008 | Gontier et al. |

FOREIGN PATENT DOCUMENTS

| EP | 0 299 107 | 1/1989 |
| EP | 0 577 516 | 1/1994 |
| EP | 1 008 344 | 6/2000 |
| EP | 1 312 373 | 5/2003 |
| EP | 1 671 535 | 6/2006 |
| JP | 2006-213636 | 8/2006 |
| JP | 2007161632 A * | 6/2007 |
| WO | WO 01/33942 | 5/2001 |
| WO | WO 2006/127525 | 11/2006 |
| WO | WO 2009/095624 | 8/2009 |

OTHER PUBLICATIONS

12865658_PCT_FR2009_050137_search report_(2010).*
Harrison et al. Journal of Agricultural and Food Chemistry, 2003, V.51, p. 2943-48.*
Zhang et al., Food Chemistry, V.106, (2008), p. 147-152 (disclosed in the IDS Jan. 2, 2014).*
Google search "how to grow sweet potatoes". (2014).*
Alkhatib et al. (Dec. 2008) "Activity of Elaeochytrin A from Ferula elaeochytris on Leukemia Cell Lines," *Phytochemistry* 69(17):2979-2983.
Bazzalo et al. (1985) "Phenolic compounds in stems of sunflower plants inoculated with *Sclerotinia sclerotiorum* and their inhibitory effects on the fungus," *Phytopathologische Zeitschrift* 112:322-332.
Beninger et al. (Mar. 2004) "A Flavanone and Two Phenolic Acids from *Chrysanthemum morifolium* with Phytotoxic and Insect Growth Regulating Activity," *J. Chem. Ecol.* 30(3):589-605.
Cole et al. (Aug. 1984) "Phenolic Acids Associated with the Resistance of Lettuce Cultivars to the Lettuce Root Aphid," *Ann. Appl. Biol.* 105(1):129-145.
Dos Santos et al. (Jan. 2005) "Analgesic Activity of Di-Caffeoylquinic Acids from Roots of Lychnophora ericoides (Arnca da serra)," *J. Ethnopharmacology* 96(3):545-549.
Hook et al. (Jan. 1993) "Leontopodium alpinum Cass. (Edlweiss): In Vitro Culture, Micropropagation, and the Production of Secondary Metabolites," In; *Biotechnology in Agriculture and Forestry*, Springer Verlag, Berlin, DE, pp. 217-232.
International Search Report and Written Opinion, Corresponding to International Application No. PCT/FR2009/050137, Mailed Aug. 6, 2010, English Translation.
International Preliminary Report on Patentability, Corresponding to International Application No. PCT/FR2009/050137, Completed Nov. 9, 2010, English Translation.
Islam et al. (May 2002) "Identification and Characterization of Foliar Polyphenolic Composition in Sweetpotato (*Ipomoea batatas* L.) Genotypes," *J. Agric Food Chem.* 50(13):3718-3722.
Islam et al. (Jan. 2003) "Distribution and Physiological Functions of Caffeoylquinic Acid Derivatives in Leaves of Sweetpotato Genotypes," *J. Food Sci.* 68:111-116.
Iwai et al. (Jul. 2004) "In Vitro Antioxidative Effects and Tyrosinase Inhibitory Activities of Seven Hydroxycinnamoyl Derivatives in Green Coffee Beans," J. Agric Food Chem. 52(15):4893-4898.
Jin et al. (2006) "Tissue Cultures and Polyphenol Production in Solidago Altissima L," *Nippon Shokuhin Kagaku* Gakkaishi 13(3):136-140, Chemical Abstracts Service, Accession No. 2007:252417.
Kabganian et al. (2002) "Localization of Alkamides, Echinacoside and Cynarin in *Echinacea angustifolia*," *J. Herbs, Spices Medicinal Plants* Chemical Abstracts Service, Accession No. 2003:664580.

(Continued)

*Primary Examiner* — Yong Chu
(74) *Attorney, Agent, or Firm* — Lathrop & Gage LLP

(57) ABSTRACT

Method for preparing 3,5-dicaffeoylquinic acid and certain derivatives thereof, and use thereof in the preparation of plant-protection products. Method for combating aphids using 3,5-dicaffeoylquinic acid and certain derivatives thereof.

19 Claims, 26 Drawing Sheets

(56) References Cited

OTHER PUBLICATIONS

Kodoma et al. (Feb. 1998) "3,5-DiO-Caffeoylquinic acid, and Infection-Inhibiting Facot from *Pyrus pyrifolia* Induced by Infection and *Alternaria alternate*," *Phytochemistry* 47(3):371-373.

Maruta et al. (Oct. 1995) "Antioxidative Caffeoylquinic Acid Derivatives in the Root of Burdock (*Arctium lappa* L.)," *J. Agric Food Chem.* 43(10):2592-2595.

Mishima et al. (Oct. 2005) "Identification of Caffeoylquinic Acid Derivatives from Brazilian Propolis as Constituents Involved in Induction of Granulocytic Differentiation of HL-60 Cells," *Bioorg. Med. Chem.* 13(20):5814-5818.

Schwarz et al. (Jun 1996) "A cyanogenic glycoside from Canthium schimperianum," Phytochemistry 42(3):633-636.

Stange, Jr. et al. (Nov. 2001) "Constituents from the Periderm and outer Cortex of *Ipomoea batatas* with Antifungal Activity against *Rhizopus stolonifer*," *Postharvest Biol. Technol.* 23(2):85-92.

Takenaka et al. (Web Release Dec. 21, 2002) "Caffeic Acid Derivatives in the Roots of Yacon (*Smallanthus sonchifolius*)," *J. Agric. Food Chem.* 51:793-796.

Tamura et al. (2004) Triterpenoid and caffeic acid derivatives in the leaves of ragweed, Ambrosia artemisiifoliaL. (Asterales: Asteraceae), as feeding stimulants of Ophraella communaLeSage (Coleoptera: Chrysomelidae) Chemoecology 14(2):113118.

Taylor et al. (1966) "Turnover and Metabolism of Chlorogenic Acid in Zanthium Leaves and Potato Tubers," *Plant Physiol.* 41:1350-1359.

Kojima et al. (1973), "Studies on Chlorogenic Acid Biosynthesis in Sweet Potato Root Tissue in Special Reference to the Isolation of a Chlorogenic Acid Intermediate", Plant Physiol. (1973) 51, 768-771.

Uritani et al. (1955), "Derivatives of Caffeic Acid in Sweet Potato attacked by Black Rot", Nature, vol. 175, p. 812.

Zheng et al. (2008), "Profiling the chlorogenic acids of sweet potato (*Ipomoea batatas*) from China", Food Chemistry 106 (2008) 147-152.

\* cited by examiner

Figure 4

|   |   | Condition<br>Medium/solution/lighting | Root solids (g) | 3,5-diCQ content (mg.g$^{-1}$ solids) | Quantity of 3,5-diCQ per plant (mg) |
|---|---|---|---|---|---|
| A |   | Liquid/water/darkness | 0.30 | 45.7 | 13.9 |
| B |   | Liquid/water/light | 0.31 | 92.0 | 28.2 |
| C | ■ | Liquid/0.05mM N sol./darkness | 0.33 | 30.9 | 10.0 |
| D |   | Liquid/6 mM N sol./darkness | 1.57 | 20.6 | 32.0 |
| E | ■ | Perlite/water/darkness | 0.68 | 36.3 | 24.9 |
| F |   | Perlite/6 mM N sol./darkness | 1.75 | 14.8 | 25.4 |

Figure 6

|   | Condition | Root solids (g) | 3,5-diCQ content (mg.g$^{-1}$ solids) | Quantity of 3,5-diCQ per plant (mg) |
|---|---|---|---|---|
|   | Medium/solution/lighting |   |   |   |
| E | Liquid/water/darkness | 0.315 | 51.13 | 16.10 |
| F | Liquid/6 mM N, 1 mM P sol./darkness | 0.677 | 25.11 | 17.38 |
| G | Liquid/0 mM N, 1 mM P sol./darkness | 0.469 | 28.11 | 12.95 |
| H | Liquid/6 mM N, 0 mM P sol./darkness | 0.445 | 35.09 | 16.85 |

Figure 8

| | Condition | | Solids (g) | | 3,5-diCQ content (mg.g$^{-1}$ solids) | | Qu. 3,5-diCQ/plant (mg) | | |
|---|---|---|---|---|---|---|---|---|---|
| | Cuttings | Layers | Cuttings | Layers | Cuttings | Layers | Cuttings | Layers | Total per plant |
| A | Water | Water | 0.36 | 0.77 | 47.4 | 31.9 | 16.8 | 24.5 | 41.3 |
| B | Water | Solution | 0.31 | 1.25 | 44.7 | 11.6 | 13.6 | 14.7 | 28.3 |
| C | Solutions | Solution | 0.99 | 1.22 | 16.2 | 10.2 | 17.4 | 13.6 | 31.0 |
| D | Solution | Water | 2.03 | 0.74 | 15.5 | 35.5 | 31.1 | 26.2 | 57.3 |

FIGURE 10

| | Molecular Weight | mM | Per 100 mL |
|---|---|---|---|
| Amino Acids (L) | | | mg |
| Alanine | 89.09 | 20.06 | 178.71 |
| β-alanine | 89.1 | 0.70 | 6.22 |
| Arginine | 174.2 | 14.06 | 244.90 |
| Asparagine $H_2O$ | 150.14 | 19.88 | 298.55 |
| Aspartic acid | 133.11 | 6.63 | 88.25 |
| Cysteine | 121.16 | 2.44 | 29.59 |
| Glutamic acid | 147.13 | 10.15 | 149.36 |
| Glutamine | 146.15 | 30.49 | 445.61 |
| Glycine | 75.07 | 22.19 | 166.56 |
| Histidine HCl $H_2O$ | 209.63 | 6.49 | 136.02 |
| Isoleucine (allo free) | 131.18 | 12.56 | 164.75 |
| Leucine | 131.18 | 17.65 | 231.56 |
| Lysine HCl | 182.65 | 19.22 | 351.09 |
| Methionine | 149.21 | 4.85 | 72.35 |
| Ornithine HCl | 168.62 | 0.56 | 9.41 |
| Phenylalanine | 165.19 | 17.83 | 294.53 |
| Proline | 115.13 | 11.23 | 129.33 |
| Serine | 105.09 | 11.83 | 124.28 |
| Threonine (allo free) | 119.12 | 10.67 | 127.16 |
| Tryptophan | 204.23 | 2.09 | 42.75 |
| Tyrosine | 181.19 | 2.13 | 38.63 |
| Valine | 117.15 | 16.29 | 190.85 |
| Total | | 260.01 | 3520.45 |
| | | | |
| Saccharose | 342.2 | 584.28 | 20000.00 |
| Saccharose/AA ratio | | 2.25 | |
| | | | |
| Vitamins | | | (mg) |
| P-aminobenzoic acid | | | 10.00 |
| L-ascorbic acid | | | 100.00 |
| Biotin | | | 0.10 |
| Calcium D-pantothenate | | | 5.00 |
| Choline chloride | | | 50.00 |
| Folic acid | | | 1.00 |
| Anhydrous i-inositol | | | 42.00 |
| Nicotinic amide | | | 10.00 |
| Pyridoxine HCl | | | 2.50 |
| Riboflavin | | | 0.50 |
| Thiamine HCl | | | 2.50 |
| | | | |
| Trace Metals | | | (mg) |
| $CuSO_4, 5H_2O$ | | | 0.47 |
| $FeCl_3, 6H_2O$ | | | 4.45 |
| $MnCl_2, 4H_2O$ | | | 0.65 |
| NaCl | | | 2.54 |
| $ZnCl_2$ | | | 0.83 |
| | | | |
| Miscellaneous | | | (mg) |
| Calcium citrate | | | 10.00 |
| Cholesterol benzoate | | | 2.50 |
| $MgSO_4\ 7H_2O$ | | | 242.00 |
| $KH_2PO_4$ | | | 250.00 |

Chlorogenic acid dose (mM)

METHOD FOR PREPARING DICAFFEOYLQUINIC ACIDS AND USE THEREOF IN COMBATING APHIDS

CROSS-REFERENCE TO RELATED APPLICATIONS

This application is a U.S. National Stage of international application PCT/FR2009/050137, filed Jan. 30, 2009, which designates the U.S. and which was not filed or published in English and claims priority to French patent application FR08/00561, filed Feb. 1, 2008. Each of these applications is incorporated by reference herein in its entirety.

The goal of this invention is the preparation of 3,5-dicaffeoylquinic acid and certain derivatives thereof, as well as their use in preparing phytosanitary products.

3,5-dicaffeoylquinic acid (3,5-diCQ) and its various derivatives have been identified in numerous species of agronomical interest belonging to various botanical families (Rosaceae, including trees that bear pome fruit and stone fruit; Solanaceae, including tomatoes and potatoes; Asteraceae, including sunflowers, artichokes, and lettuce; Rubiaceae, including coffee; Convolvulaceae, including sweet potatoes, etc.).

Several hundred publications describe the presence of these substances in these various species and discuss their chemical and biological properties.

These compounds offer considerable antioxidant activity, which makes them very interesting from a nutritional perspective (Ohnishi et al, (1994) Phytochemistry, 36: 579-583; Iwai et al, (2004) Journal of Agricultural and Food Chemistry, 52: 4893-4898; Kim & Lee, (2005) Planta Medica, 71: 871-876; Saito et al; (2005) Bioorganic & Medicinal Chemistry, 13: 4191-4199).

They also present many medicinal properties; among others, as analgesics (dos Santos et al, (2005) Journal of Ethnopharmacology 96: 545-549), antihypertensives (Mishima et al, (2005a) Biological & Pharmaceutical Bulletin 28: 1909-1914), hypouricemics (Nguyen et al, (2005) Biological & Pharmaceutical Bulletin 28: 2231-2234), hepatoprotectives (Basnet et al, (1996) Biol Pharm Bull 19: 1479-1484), antiinflammatories (Peluso et al, (1995) Journal of Natural Products 58: 639-646), and cancer-fighting drugs (Mishima et al, (2005b) Bioorganic & Medicinal Chemistry 13: 5814-5818).

These compounds are present in preparations used in traditional medicine, in commercially-available plant extracts (artichoke- and echinacea-based extracts), and in propolis (Mishima et al, (2005a) Biological & Pharmaceutical Bulletin 28: 1909-1914; Mishima et al, (2005b) Bioorganic & Medicinal Chemistry 13: 5814-5818; Basnet et al, (1996) Biol Pharm Bull 19: 1479-1484). They also have major antiinfectious—specifically, antiviral—properties. They constitute a new class of antiretrovirus, in particular for treating AIDS, through their inhibitory activity on HIV integrase (Mahmood et al, (1993) Antiviral Chem. Chemother. 4: 235-240; McDougall et al, (1998) Antimicrobial Agents & Chemotherapy 42: 140-146; Zhu et al, (1999) J Virol 73: 3309-3316).

Patent EP 1008344 describes the use of this group of molecules in treating hepatitis B; international patent application WO2006127525 describes their use in treating AIDS; Japanese patent application JP2006213636 describes the use of this group of molecules in treating cancer; patent application EP0577516 describes depigmenting dermatological compositions containing them; and patent application EP1312373 discusses their antiallergic effects.

The fungicidal properties of these molecules have also been frequently shown (Bazzalo et al, (1985) Phytopathologische Zeitschrift 112: 322-332; Kodoma et al, (1998) Phytochemistry 47: 371-373; Stange et al, (2001) Postharvest Biology & Technology 23: 85-92).

Conversely, the insecticidal properties of this group of molecules have been much less studied and the results are highly conflicting. While certain authors have established a correlation between the high diCQ content in the roots of lettuce cultivars and their resistance to an aphid (*Pemphigus bursarius*), they have never shown the direct biological activity of these molecules on the insect (Cole et al. (1984) Annals of Applied Biology 105: 129-145). Other authors have shown that certain derivatives have little or no insecticidal activity on chewing insects (Beninger et al, (2004) J Chem Ecol 30: 589-605; Schwarz et al. (1996) Phytochemistry 42(3):633-636). Certain authors have even shown a phagostimulating effect of 3,5-diCQ on chewing insects (Tamura et al. (2004) Chemoecology 14(2):113-118; Mullin et al. (1991) J of Agricultural & Food Chemistry 39(12):2293-2299).

The peach tree *Prunus persica* (L.) Batsch (Rosaceae), a tree that is especially well-suited to the Mediterranean climate, is primarily grown in China, North America (California), South America (Chile and Argentina), and in Europe in the countries lining the Mediterranean Basin, where the main crop-growing areas are Spain, Italy, Greece, and France. In 2004, world peach production was 15.6 million tons, distributed over a surface area of 1.4 million hectares. French production during this same year was 413,000 tons produced mainly throughout the Rhone Valley, in Provence, in Roussillon, and throughout the Garonne Valley. For these southern regions, this crop represents a major economic issue.

However, peach trees are often attacked by animal or microbial parasites. The main pathogens and pests affecting peach trees are fungi: oidium (*Sphaerotheca pannosa*), peach leaf curl (*Taphrina deformans*), and brown rot (*Monilinia laxa, M. fructigena*, and *M. fructicola*); bacteria that can cause blight (*Xanthomonas arboricola* pathovar *pruni*), and many insects and viruses.

One especially troublesome attack is launched by the green peach aphid, *Myzus persicae* (Sulzer). This piercing/sucking insect is particularly harmful, not only due to the direct damage that it causes but also because it is a potential vector for the plum pox virus, the causal agent for Sharka disease, which causes fruit deformation and discoloration, thereby making them unfit for sale. Since no curative means for combating the insect are available, infected trees must be uprooted.

In order to combat this parasite, the farmer must confront two issues:
- fighting the green peach aphid with chemicals, which requires powerful (often noxious and toxic) insecticides and whose effectiveness is random in nature, carries the risk of resistance appearing in *Myzus persicae* (Guillemaud et al, (2003) Bulletin of Entomological Research 93, 289-297) and
- concern for the environment, which seeks to reduce phytosanitary inputs.

These issues have led geneticists and entomologists to attempt to improve the peach tree's resistance to *Myzus persicae*.

The green peach aphid belongs to the Hemiptera order and to the Aphididae family. It measures 1.2 to 2.5 mm long. It is a phytophagic aphid that feeds on phloem sap, taken from the phloem by piercing/sucking-type mouth parts (Hullé et al, (1998) in ACTA and INRA publications, 77 pages).

The annual cycle of *Myzus persicae*, in a temperate climate, is composed of a sexual reproduction phase, leading to the laying of a diapausing winter egg, followed by a parthenogenetic reproduction phase (full cycle or holocyclic). These two phases occur on different host plants (dioecious cycle), referred to respectively as the primary host (peach tree) and secondary host (herbaceous plants, some of which are of great economic importance: potatoes, cabbage, eggplant, beets, etc.).

The winter eggs laid at the base of peach tree buds hatch from late January to late April, during budbreak, and yield wingless parthenogenetic females, the fundatrices. These fundatrices are the starting point for several generations of parthenogenetic females, the nymphs, on the primary host. In late spring and in summer, when the peach tree is overpopulated, the nymphs give birth to winged individuals that colonize their secondary host. These winged individuals will engender, via asexual reproduction, several generations of wingless or winged aphids, the virginoparae, which in the fall give birth to sexed and winged male and female individuals, the sexuparae. These individuals will return to the peach tree in order to lay winter eggs (Hullé et al, (1998) cited above; Sauge, (1999) Analyse des mécanismes de résistance du pêcher Prunus persica (L.) Batsch au puceron vert [Analysis of Mechanisms for Green Aphid Resistance in the Prunus persica Peach Tree (L.) Batsch]; Thesis, Université Pierre et Marie Curie (Paris 6) 188 pages).

The direct damage caused by this aphid is due to the latter's bites while feeding, which cause buds to dry out, flowers to drop off, and deformations to occur in leaves and young shoots; they also disrupt growth and may induce necrotic reactions (Massonié et al, (1979) Revue de zoologie agricole et pathologie végétate [Review of Agricultural Zoology and Plant Pathology] 78, 1-5; Monet and Massonié, (1994) Agronomie 2 177-182; Monet and Guye, (1998) in Monet R. (Ed) Proc. Fourth Intern. Peach Symposium Acta Hort 171-175). Moreover, Myzus persicae, as was mentioned previously, is a vector for the plum pox virus (which causes Sharka disease), belonging to the group of potyviruses that cause indirect damage, leaf discoloration, and fruit deformation.

In light of the preceding, it is necessary to find novel treatments for combating aphids, specifically the green peach aphid (Myzus persicae), that are effective yet environmentally-friendly.

The inventors have brought to light the repulsive and toxic effect of 3,5-diCQ and of some derivatives thereof on various aphid species.

However, 3,5-diCQ and its isomers, apart from 1,3-diCQ (or cynarin), isolated from artichokes, are not widely available. Hence, these compounds must be extracted from various plants. In addition to artichokes, we may cite coffee (EP0299107) and sunflowers, in which the overproduction of phenolic compounds has been described, and more specifically, the overproduction of dicaffeoylquinic acids, by using a biotic elicitor, the pathogen Sclerotinia (EP 1671535).

Therefore, a pressing need exists for developing methods for obtaining easy-to-use, high-yield 3,5-diCQs and derivatives thereof.

The inventors have therefore sought to purify this molecule in sufficient quantities. Isolating 3,5-diCQ and derivatives thereof from peach trees did not appear satisfactory due to the relatively low content of the substance and the presence of numerous phenolic compounds that might hinder purification (FIG. 1). Conversely, Ipomoea batatas (Convolvulaceae), whose phenolic composition has been studied in the edible tuber (sweet potato) and in its leaves by Japanese teams (Islam et al, (2002) Journal of Agricultural and Food Chemistry 50: 3718-3722; Islam et al, (2003) Journal of Food Science 68: 111-116), has proven to be a promising source.

The nontuberized roots of Ipomoea batatas have been shown to contain large amounts of 3,5-diCQ (approximately 15 mg per g of solids) and low amounts of contaminating isomeric forms (FIG. 2). These amounts are especially high under mineral deficiency conditions, specifically nitrogen, and when the roots are grown under light. The amounts may run as high as 90 mg per g of solids when grown on distilled water under light.

Hence, the goal of this invention is a method for preparing compounds of Formula (I)

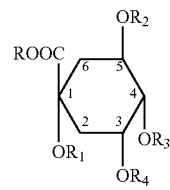

wherein
R represents a hydrogen atom or a methyl group,
$R_1$, $R_2$, and $R_4$ each represent, independently of each other, a hydrogen atom or a caffeoyl group and
$R_3$ represents a hydrogen, a caffeoyl group, or a succinyl group, provided that at least two of $R_1$ through $R_4$ represent a caffeoyl group, and that $R_3$ represents a succinyl group only if $R_2$ and $R_4$ represent a caffeoyl group,
from nontuberized roots comprising the following steps:
a) taking samples of the nontuberized roots or recovering the root exudate,
b) extraction of phenolic compounds using one or several organic solvents,
c) recovery of the raw extract,
d) optional purification of said extract obtained in Step c)
e) optionally, spontaneous isomerization of said extracts under alkaline pH conditions; said Formula (I) compounds may be in the form of regio- or stereoisomers, or mixtures thereof.

By "nontuberized root," we mean a root of normal structure, excluding the parts involving the tuberization phenomenon, which is characterized by the accumulation of reserves and thickening of the root and leads to the formation of an edible tuber. In the case of Ipomoea batatas, the edible tuber is widely referred to as a sweet potato.

By "caffeoyl group," we mean the group represented by the following formula

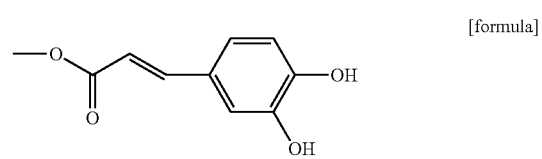

[formula]

In an advantageous embodiment of the invention, these compounds are extracted from the nontuberized root of a plant, specifically of a plant from the Ipomoea (Convolvulaceae) genus or from the genera of the same family Argyreia, Calycobolus, Calystegia, Convolvulus, Dichondra, Erycibe, Evolvulus, Iseia, Jacquemontia, Maripa, Merremia, Mina, Operculina, Porana, Stictocardia, or Turbina. In addition to Ipomoea batatas, the Ipomoea genus comprises approximately 500 species, including ornamental plants such as morning glory (Ipomoea purpurea) or edible plants such KangKong or water spinach (*Ipomoea aquatica*) that are consumed in Asia. The *Convolvulus* genus comprises approximately 250 species, including field bindweed (*Convolvulus arvensis*) and dwarf morning glory (*Convolvulus tricolor*). The *Calystegia* genus comprises approximately 25 species, including hedge bindweed (*Calystegia sepia*) and giant bindweed (*Calystegia silvatica*).

Specifically, 3,5-dicaffeoylquinic acid and derivatives thereof are extracted from the nontuberized roots of a plant selected from the group comprising the sweet potato (*Ipomoea batatas*), morning glory (*Ipomoea purpurea*), water spinach (*Ipomoea aquatica*), oceanblue morning glory (*Ipomoea indica*), Scarlett O'Hara morning glory (*Ipomoea nil*), and hedge bindweed (*Calystegi sepium*).

In an advantageous embodiment of the method of the invention, 3,5-dicaffeoylquinic acid and derivatives thereof are extracted from nontuberized *Ipomoea batatas* roots.

Nontuberized *Ipomoea batatas* roots may be produced from seedlings, cuttings, layers, or tubers, grown in hydroponic culture using the technique described in international patent application WO 01/33942, on a horticultural substrate or in open soil, advantageously under mineral deficiency conditions. They may be harvested once their quantity is sufficient for proceeding with 3,5-diCQ extraction.

Advantageously, the nontuberized roots are produced by being grown in a liquid medium, under light, and under mineral deficiency conditions.

In an advantageous embodiment of the invention, the compounds of Formula (I),

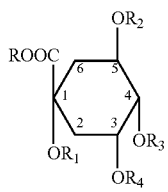

which are prepared, are selected from 3,5-dicaffeoylquinic (3,5-diCQ) acid, the various isomeric forms of 3,5-diCQ, specifically cynarin (1,3-diCQ), 1,5-dicaffeoylquinic (1,5-diCQ) acid, 3,4-dicaffeoylquinic (3,4-diCQ) acid, and 4,5-dicaffeoylquinic (4,5-diCQ) acid, its triacylated analogues such as 3,4,5-tricaffeoylquinic (3,4,5-triCQ) acid, its methylated analogues such as methyl 3,5-dicaffeoylquinate, methyl 3,4-dicaffeoylquinate, methyl 4,5-dicaffeoylquinate, and 4-succinyl-3,5-dicaffeoylquinic acid.

In an especially advantageous embodiment of the invention, the method for preparing Formula (I) compounds, specifically 3,5-dicaffeoylquinic acid, comprises the following steps:

a) taking samples of *Ipomoea batatas* roots originating from tubers, cuttings, seedlings, or layers, b) freezing the roots sampled in Step a) in liquid nitrogen, c) freeze-drying the roots frozen in Step b), d) grinding the freeze-dried roots in liquid nitrogen, then freeze-drying them in order to obtain a dry powder, e) extracting phenolic compounds using an organic solvent in 1 to 4 passes, via cold stirring, f) rinsing the final residue from step e) with the same organic solvent as the one used in Step e), then evaporating the solvent present in the extract until an aqueous phase is obtained, g) optionally, liquid/liquid volume-to-volume extraction using an apolar solvent, via several successive extractions, after adding a salt and an acid during the aqueous phase in order to facilitate the extraction of DiCQs in the apolar solvent, h) dry concentration of the aqueous phase obtained in Step f) or of the organic phase obtained in optional Step g), after adding a drying agent in order to eliminate the residual water and filtration, then taking up the dry residue using an organic solvent, i) separation using semipreparative reversed-phase HPLC and collection of the fraction containing 3,5-diCQ, j) concentration of the fraction obtained in step i) until an aqueous phase is obtained, k) liquid/liquid extraction using an organic (volume-to-volume) solvent via several successive extractions after adding a salt, in the aqueous phase in order to facilitate 3,5-diCQ extraction in the apolar solvent, l) dry concentration of the organic phase, after a drying agent is added, and filtration in order to eliminate the residual water, and taking up using an organic solvent, m) cold precipitation of the molecule by adding water (at least 3 volumes for 1 volume of the organic solvent used in the previous step), freezing of the extract in liquid nitrogen, and freeze-drying in order to obtain the molecule in the form of a dry powder.

In an advantageous embodiment of the invention, the organic solvents used in Step e) are those that are traditionally used in plant extraction; specifically, they are selected from the group comprising ethanol, methanol, and acetone; these solvents may be mixed with water, e.g., the 70% ethanol used in Example 1.

In an especially advantageous embodiment of the invention, Step g) is carried out by extracting with ethyl acetate or diethylether (volume-to-volume) after adding NaCl or ammonium sulfate (8% saturation) and metaphosphoric acid (1-2% weight/final volume), as per the protocols designed by Macheix (1974), Doctoral Thesis in Natural Sciences, Université Paris VI, 168 pp.

The solvent evaporation steps are performed using any traditionally-used technique, e.g., using a rotary evaporator, and the drying agent used in steps h) and l) is advantageously anhydrous sodium sulfate.

The organic solvent used in step h) is generally the one used for the semipreparative chromatography of Step i) and is advantageously HPLC-purity methanol.

The semipreparative chromatography of step i) is advantageously performed on a C18 column by a water-acidified-to-pH-2.6/methanol gradient.

The method of the invention yields 3,5-dicaffeoylquinic acid with a purity higher than 90%, advantageously ranging from 93 to 95%. Contaminating substances are essentially 3,5-diCQ isomers.

In an advantageous embodiment of the invention, in order to better preserve during extraction the indigenous isomeric forms that are initially present in the plant tissues, all of steps a) through m) are performed under cold conditions, preferably at a temperature ranging from 3 to 5° C., protected from prolonged light exposure, and the acid pH of the aqueous solvents preferably ranges from 5.0 to 6.0.

3,4-dicaffeoylquinic (3,4-diCQ) and 4,5-dicaffeoylquinic (4,5-diCQ) acids can be easily produced from 3,5-dicaffeoylquinic acid via spontaneous isomerization under alkaline pH conditions. Hence, isomerization of 3,5-diCQ can be performed in a Tris-HCl buffer (50 mM), pH 8.5, for 2 hours at 40° C. using a method designed by Hanson (1965) Biochemistry 4: 2719-2731, and Moller and Herrmann (1982) Journal of Chromatography 241: 371-379. Under these conditions, the three isomeric forms are present in comparable amounts and can be separated by semipreparative HPLC according to a protocol that is identical to the one used for purifying 3,5-diCQ.

Another goal of this invention is the use of at least one Formula (I) compound or mixtures thereof in combating aphids.

According to the invention, the Formula (I) compounds are used in the form of a composition that comprises an effective quantity of said compounds.

By "an effective quantity" of at least one compound selected from 3,5-dicaffeoylquinic (3,5-diCQ) acid, the various isomeric forms of 3,5-diCQ, specifically cynarin (1,3-diCQ), 1,5-dicaffeoylquinic (1,5-diCQ) acid, 3,4-dicaffoylquinic (3,4-diCQ) acid, and 4,5-dicaffeoylquinic (4,5-diCQ) acid, its triacylated analogues such as 3,4,5-tricaffeoylquinic (3,4,5-triCQ) acid, its methylated analogues such as methyl 3,5-dicaffeoylquinate and 4-succinyl-3,5-dicaffeoylquinic acid, we mean either raw extracts or purified extracts; said extracts may be in either liquid or solid form, or any preparations containing said extracts.

In an advantageous embodiment of the invention, the preferred mixture is the mixture of 3,5-diCQ, 3,4-diCQ, and 4,5-diCQ.

The compositions used in the method of the invention comprise at least one dicaffeoylquinic acid, its triacylated analogues, its methylated analogues, 4-succinyl-3,5-dicaffeoylquinic acid, or a mixture thereof at a concentration ranging from 0.01 to 5 mM, advantageously from 0.1 to 2 mM, more advantageously from 0.25 to 1 mM.

In an advantageous embodiment of the invention, the aphids are selected from the group comprising *Myzus persicae* (green peach aphid), *Myzus varians* (peach leaf-roll aphid), *Myzus cerasi* (black cherry aphid), *Brachycaudus persicae* (black peach aphid), *Aphis pomi* (nonmigrating green apple aphid), *Brachycaudus helichrysi* (plum leaf-curl aphid), *Hyalopterus pruni* (mealy plum aphid), *Dysaphis plantaginea* (rosy apple aphid), *Dysaphis pyri* (pear-bedstraw aphid), *Aphis gossypii* (melon aphid or cotton aphid), *Acyrthosiphum pisum* (pea aphid), *Macrosiphum euphorbiae* (pink and green potato aphid), *Aphis spiraecola* (=A. citricola) (green citrus aphid), *Aphis fabae* (black bean aphid), *Rhopalosiphum maidis* (green maize aphid), *Rhopalosiphum padi* (bird cherry oat aphid), *Sitobion avenae* (grain aphid), *Diuraphis noxia* (Russian wheat aphid), *Brevicoryne brassicae* (cabbage aphid), *Eriosoma lanigerum* (woolly apple aphid), *Nasonovia ribisnigri* (lettuce aphid), *Amphorophora idaei* (large raspberry aphid), *Toxoptera aurantii* (black citrus aphid and coffee tree aphid), *Elatobium abietinum* (green spruce aphid), and *Pemphigus bursarius* (lettuce root aphid).

In an especially advantageous embodiment of the invention, the aphid is *Myzus persicae* (green peach aphid).

The compositions used in the method of the invention are applied onto the aphids or onto a location inhabited by said aphids.

Another goal of this invention is a method for combating aphids that includes the application of at least one Formula (I) compound or a mixture thereof onto the aphids or onto a location inhabited by said aphids.

Examples 1 through 6 and FIGS. 1 through 24, which follow, illustrate the invention.

FIG. 1 shows the 330 nm HPLC chromatogram of a peach tree apex extract (5 CQ: 5-caffeoylquinic acid or chlorogenic acid, metabolic precursor of 3,5-diCQ). Peaks a, b, and c represent chlorogenic acid, the internal control, and 3,5-diCQ, respectively. KONTRON HPLC analysis chain: 2 micro pumps 420, sample injector-changer 460, double wavelength UV detector 430. Piloting and acquisition using DIAMIR software. MERCK LiChro CART 250-4—Superspher 100 RP18 endcapped column, length 250 mm, diameter 4 mm, placed in an oven set at 30° C. Mobile phase: solvent A: ultrapure water acidified to pH 2.6 with orthophosphoric acid, solvent B: HPLC-quality methanol. Injection: 10 µl of extract solubilized in methanol, filtered on PTFE membrane, 0.45 µm. Detection at 330 and 280 nm.

The elution gradient is as follows:

| | Time (min.) | Flow rate ml/min. | % A | % B |
|---|---|---|---|---|
| Acquisition | 0.00 | 0.5 | 97 | 3 |
| | 5.00 | 0.5 | 97 | 3 |
| | 13.00 | 0.5 | 92 | 8 |
| | 23.00 | 0.5 | 88 | 12 |
| | 30.00 | 0.5 | 88 | 12 |
| | 33.00 | 0.5 | 87 | 13 |
| | 38.00 | 0.5 | 87 | 13 |
| | 40.00 | 0.5 | 86 | 14 |
| | 46.00 | 0.5 | 86 | 14 |
| | 50.00 | 0.5 | 84 | 16 |
| | 55.00 | 0.5 | 84 | 16 |
| | 57.00 | 0.5 | 83 | 17 |
| | 67.00 | 0.5 | 83 | 17 |
| | 82.00 | 0.5 | 81 | 19 |
| | 87.00 | 0.5 | 79 | 21 |
| | 95.00 | 0.5 | 79 | 21 |
| | 105.00 | 0.5 | 77 | 23 |
| | 107.00 | 0.5 | 77 | 23 |
| | 109.00 | 0.7 | 77 | 23 |
| | 115.00 | 0.7 | 77 | 23 |
| | 170.00 | 0.5 | 40 | 60 |
| | 171.00 | 0.5 | 40 | 60 |
| | 173.00 | 0.5 | 40 | 60 |
| | 175.00 | 0.5 | 40 | 60 |
| Rinsing | 180.00 | 0.5 | 97 | 3 |
| | 210.00 | 0.5 | 97 | 3 |

Under these conditions, the retention time of 3,5-diCQ is approximately 142 min.

FIG. 2 shows various HPLC chromatograms of certain extracts.

FIG. 2A shows the 330 nm HPLC chromatogram of a nontuberized *Ipomoea batatas* root extract (5 CQ: 5-caffeoylquinic acid or chlorogenic acid). HPLC conditions are identical to those in FIG. 1. Peaks a, b, and c represent chlorogenic acid, the internal control, and 3,5-diCQ, respectively.

FIG. 2B shows the 280 nm HPLC chromatogram of a nontuberized *Ipomoea aquatica* root extract. HPLC conditions are identical to those in FIG. 1. Peaks a, b, c, and d represent chlorogenic acid, the internal control, 3,4-diCQ, and 3,5-diCQ, respectively.

FIG. 2C shows the 280 nm HPLC chromatogram of a nontuberized *Ipomoea indica* root extract. HPLC conditions are identical to those in FIG. 1. Peaks a, b, and c represent chlorogenic acid, the internal control, and 3,5-diCQ, respectively.

FIG. 2D shows the 280 nm HPLC chromatogram of a nontuberized *Calystegia sepium* root extract. HPLC conditions are identical to those in FIG. 1. Peaks a, b, c, d, and e represent chlorogenic acid, the internal control, 3,4-diCQ, 3,5-diCQ, and 4,5-diCQ, respectively.

FIG. 2E shows the 280 nm HPLC chromatogram of a nontuberized, "Scarlett O'Hara" variety, *Ipomoea nil* root extract. HPLC conditions are identical to those in FIG. 1. Peaks a, b, and c represent chlorogenic acid, the internal control, and 3,5-diCQ, respectively.

FIG. 3 shows the 330 nm HPLC chromatogram of 3,5-diCQ purified from nontuberized *Ipomoea batatas* roots. 3,4-diCQ, a and b are isomers of 3,5-diCQ. KONTRON HPLC analysis chain: 2 micro pumps 420, sample injector-changer 460, double wavelength UV detector 430. Piloting and acquisition using DIAMIR software. MERCK LiChro CART 250-4—Superspher 100 RP18 endcapped column, length 250 mm, diameter 4 mm, placed in an oven set at 30° C. Mobile phase: solvent A: ultrapure water acidified to pH 2.6 with orthophosphoric acid, solvent B: HPLC-quality methanol. Injection: 10 µl of extract solubilized in methanol, filtered on PTFE membrane, 0.45 µm. Detection at 330 and 280 nm.

Elution Gradient:

|  | Time (min.) | Flow rate ml/min. | % A | % B |
|---|---|---|---|---|
| Acquisition | 0.00 | 0.7 | 65 | 35 |
|  | 1.00 | 0.7 | 65 | 35 |
|  | 23.00 | 0.7 | 62 | 38 |
|  | 30.00 | 0.7 | 62 | 38 |
|  | 35.00 | 0.7 | 0 | 100 |
|  | 40.00 | 0.7 | 0 | 100 |
| Equilibration | 41.00 | 0.7 | 65 | 35 |
|  | 51.00 | 0.7 | 65 | 35 |

Under these conditions, the 3,5-diCQ is eluted at a time of 18 to 20 min.

FIG. 4 illustrates the influence of growing conditions on the quantity of root solids produced (MS), the 3,5-diCQ content in the roots, and quantity of 3,5-diCQ produced per cutting in the roots after growing for 4 weeks (average of 5 cuttings) (Example 2, Experiment A).

FIG. 5 shows the influence of growing conditions on (A) the quantity of root solids produced, (B) the 3,5-diCQ content in the roots, and (C) the quantity per cutting of root 3,5-diCQ produced after growing for 4 weeks (average of 5 cuttings). The growing conditions for the cuttings are listed in Table I of Example 2 (Experiment A). The vertical bars represent the standard deviation. The averages followed by the same letter are not significantly different at the 5% threshold (Tukey test).

FIG. 6 shows the influence of mineral deficiency conditions (nitrogen and phosphate) on the quantity of root solids produced, the 3,5-diCQ content in the roots, and the quantity per cutting of 3,5-diCQ produced in the roots after growing for 3 weeks (average of 3 cuttings) (Example 2, Experiment B).

FIG. 7 shows the influence of mineral deficiency conditions (nitrogen and phosphate) on (A) the quantity of root solids produced, the 3,5-diCQ content in the roots, (B) the quantity of 3,5-diCQ produced in the roots, and (C) the quantity per cutting of root 3,5-diCQ produced after growing for 3 weeks (average of 3 cuttings) (Experiment B). The growing conditions for the cuttings are listed in Table II of Example 2. The vertical bars represent the standard deviation. The averages following by the same letter are not significantly different at the 5% threshold (Tukey test).

FIG. 8 illustrates the development of a root production system involving layering. It shows the influence of the cutting and layering media on the quantity of solids produced, the 3,5-diCQ content, and the quantity per plant of 3,5-diCQ of roots originating from cuttings (grown for 4 weeks) and from layers (grown for 2 weeks) (average of 3 cuttings).

FIG. 9 illustrates the development of a root production system involving layering. It shows the influence of the cutting and layering media on (A) the quantity of solids produced, (B) the 3,5-diCQ content, and (C) the quantity per plant of 3,5-diCQ of roots originating from cuttings (grown for 4 weeks) and from layers (grown for 2 weeks) (average of 3 cuttings). The plants' growing conditions are listed in Table IV of Example 3. The growing media are distilled water or complete mineral solution with 6 mM of nitrogen (composition in Table III of Example 2). The vertical bars represent the standard deviation. The averages followed by the same letter are not significantly different at the 5% threshold (Tukey test).

FIG. 10 gives the composition of the base medium, referred to as Ap3, used in examples 2 and 3.

FIG. 11 illustrates the device used for evaluating aphid larvae behavior when selecting between two media of differing composition (Chen, (1996), Thesis, Institut National des Sciences Appliquées, Lyon, France: 158 p.).

FIG. 12 illustrates the phagostimulation index in relation to *Myzus persicae* of chlorogenic acid (A), of para-coumaric acid (B), of caffeic acid (C), of cynarin (D), of caffeic acid methyl ester (E), and of 3,5-dicaffeoylquinic acid (F) dissolved at various concentrations in the Ap3 reference medium and tested against the Ap3 medium (selection tests). The repulsive effect (negative phagostimulation index) is significant for the experiment points marked by one asterisk ($P<0.05$), by two ($P<0.01$), or by three ($P<0.001$) (Wilcoxon rank tests). The 0 mM dose corresponds to the Ap3 control medium.

FIG. 13 illustrates the phagostimulation index of 3,5-dicaffeoylquinic (3,5-diCQ) acid and of its precursor, chlorogenic acid (CA) in relation to *Myzus persicae*, tested against the Ap3 control medium or against each other. The repulsive effect (negative index) is significant for the experiment points marked by one asterisk ($P<0.05$), by two ($P<0.01$), or by three ($P<0.001$) (Wilcoxon rank tests). The 0 mM concentration (black square) corresponds to the Ap3 control medium.

FIG. 14 illustrates the phagostimulation index of 3,5-dicaffeoylquinic (3,5-diCQ) acid at 0.5 mM versus decreasing molarities of its precursor, chlorogenic acid (CA) in relation to *Myzus persicae*. The repulsive effect (negative index) is significant for the experiment points marked by one asterisk ($P<0.05$), by two ($P<0.01$), or by three ($P<0.001$) (Wilcoxon rank tests).

FIG. 15 illustrates the phagorepulsive effect on *M. persicae* of 3,5-dicaffeoylquinic (3,5-diCQ) acid (A), of the 4,5-diCQ isomer (B), and of the 3,4-diCQ/3,5-diCQ/4,5-diCQ mixture (C) in relation to the Ap3 control medium. For the isomer mixture, the dose indicates the total diCQ content. The repulsive effect (negative phagostimulation index) is significant for the experiment points marked by one asterisk ($P<0.05$), by two ($P<0.01$), or by three ($P<0.001$) (Wilcoxon rank tests). The 0 dose corresponds to the Ap3 medium.

Figure 20:
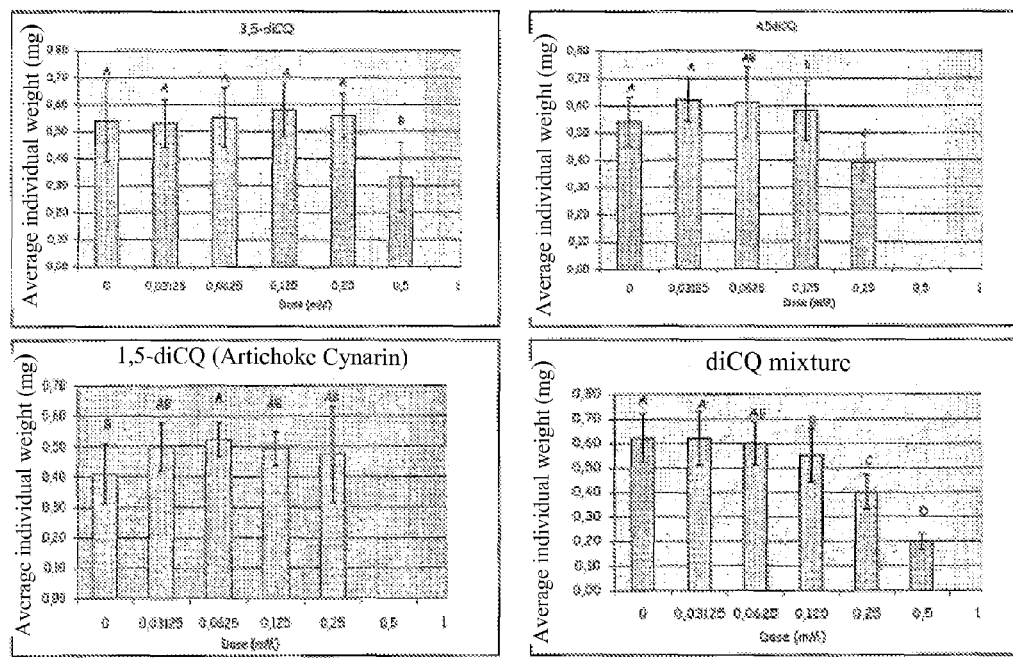

FIG. 20 illustrates the average weight (average±1 standard deviation) of an aphid that has reached the wingless adult stage at the end of larval development on the Ap3 feeding medium, supplemented or not supplemented by 3,5-dicaffeoylquinic acid, its isomers (4,5-diCQ, 1,5-diCQ), and the 3,4-diCQ/3,5-diCQ/4,5-diCQ mixture. The averages followed by the same letter are not significantly different at the 5% threshold (Bonferroni/Dunn test).

Figure 21:
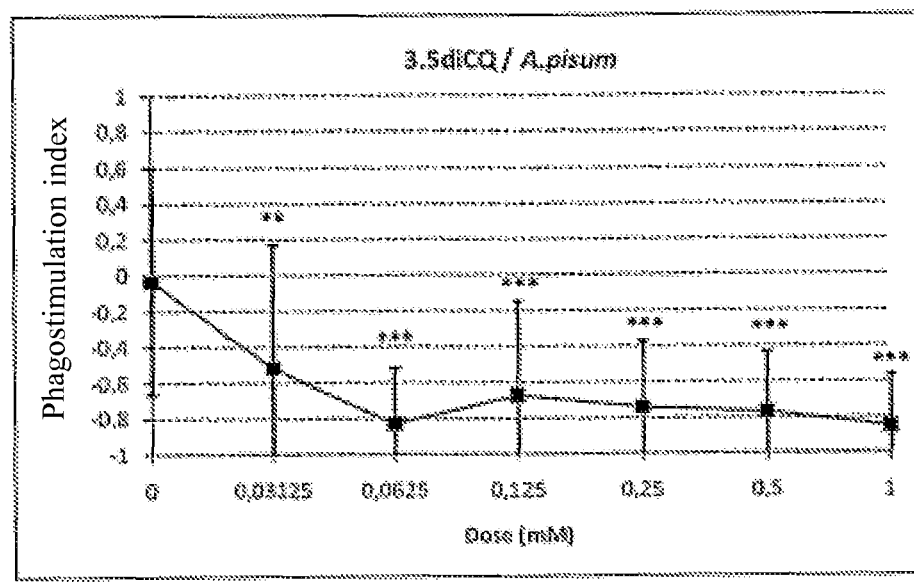

FIG. 21 illustrates the phagorepulsive effect of 3,5-dicaffeoylquinic acid on *Acyrtosiphon pisum*. The repulsive effect (negative phagostimulation index) is significant for the experiment points marked by one asterisk (P<0.05), by two (P<0.01), or by three (P<0.001). The 0 dose corresponds to the Ap3 medium.

Figure 22:
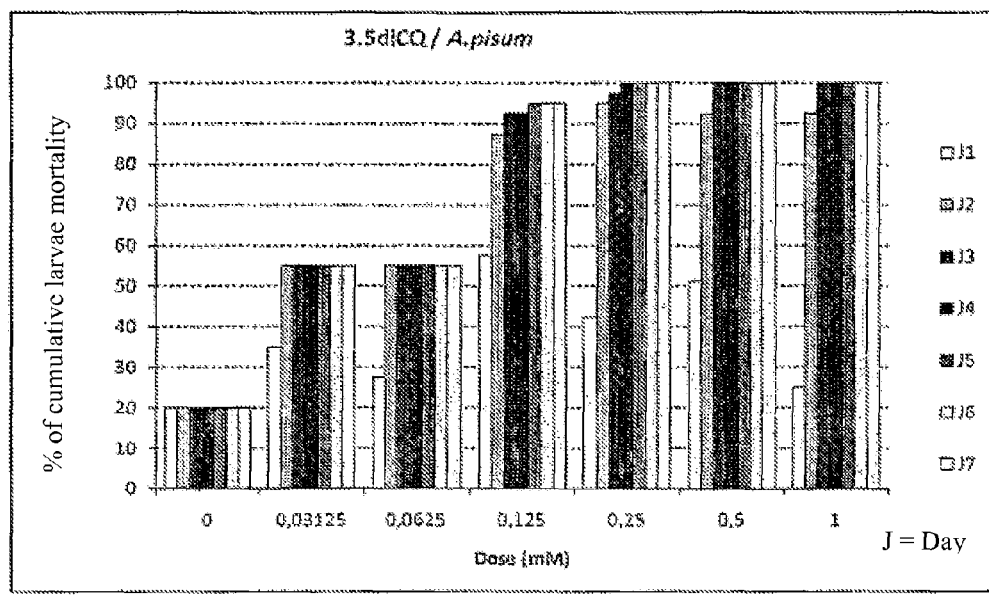

FIG. 22 illustrates the cumulative daily mortality observed during larval development of *Acyrtosiphon pisum* in the presence of 3,5-dicaffeoylquinic acid. The concentration range of 3,5-diCQ varies from 0.03125 mM to 1 mM. Dose 0 corresponds to the Ap3 control medium alone.

Figure 23:
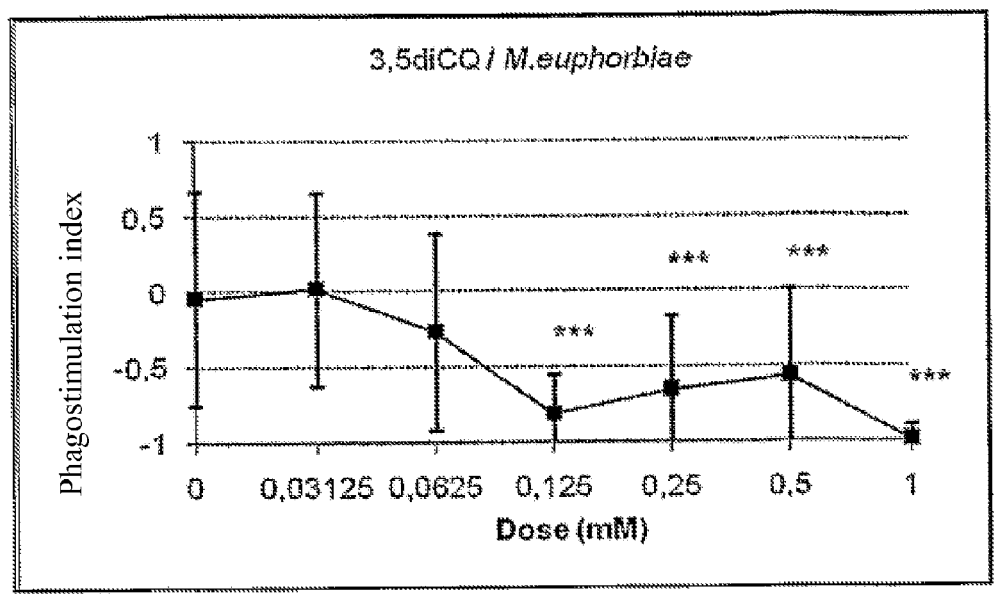

FIG. 23 illustrates the phagorepulsive effect of 3,5-dicaffeoylquinic acid on *Macrosiphum euphorbiae*. The repulsive effect (negative phagostimulation index) is significant for the experiment points marked by one asterisk (P<0.05), by two (P<0.01), or by three (P<0.001). The 0 dose corresponds to the Ap3 medium.

Figure 24:
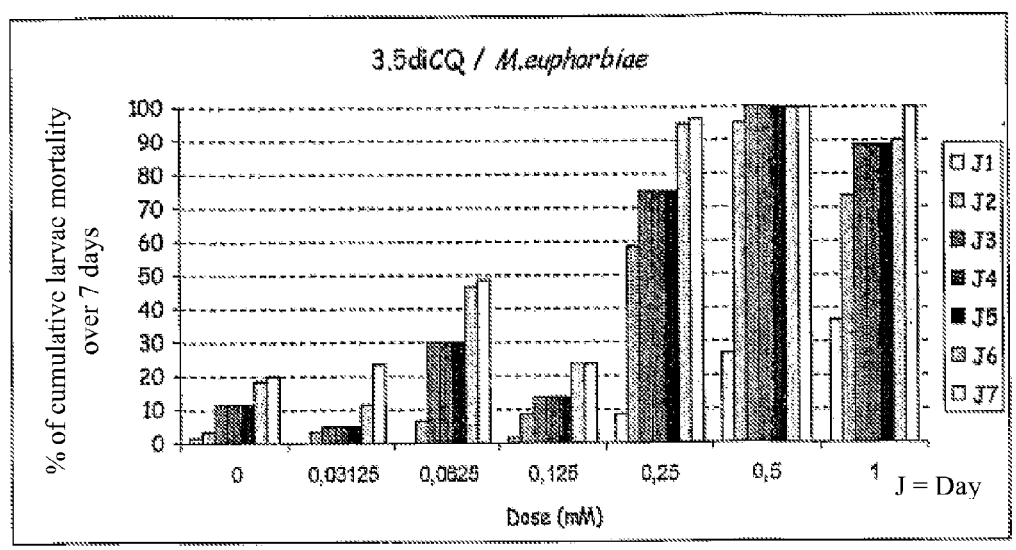

FIG. 24 illustrates the cumulative daily mortality observed during larval development of *M. euphorbiae* in the presence of 3,5-dicaffeoylquinic acid. The concentration range of 3,5-diCQ varies from 0.03125 mM to 1 mM. Dose 0 corresponds to the Ap3 control medium alone.

EXAMPLE 1

Extraction of 3,5-diCQ Acid from the Nontuberized Root of *Ipomoea batatas*

Commercially-purchased sweet potato (*Ipomoea batatas*) tubers were cultivated. The cultivation support is composed of a receptacle that holds approximately 1.5 L, protected from light. The receptacles are filled with distilled water and the tubers are 80% submerged inside them. They are grown in the laboratory under natural light.

The nontuberized roots formed by the tubers are sampled approximately 7 months after they are cultivated, immediately frozen in liquid nitrogen, and freeze-dried. Next, the roots are ground inside a mortar cooled by liquid nitrogen, then freeze-dried again in order to obtain a dry powder. This powder is kept at −20° C.

10 g of dry powder is extracted three times with 70% ethanol with, during each extraction, Ultra-Turrax homogenization of the powder or of the residue in approximately 80 mL of solvent; this is followed by 15 min. of stirring in a cold room (4° C.) and filtration on sintered glass. After the final extraction, the residue is rinsed with 60 mL of 70% ethanol. The total volume of the hydroalcoholic extract is therefore approximately 300 mL. The ethanol is evaporated using a rotary evaporator in order to obtain an aqueous phase of 10 to 20 mL to which distilled water is added until a volume of 50 mL is reached. This aqueous phase is extracted with 100 mL of ethyl acetate after adding sodium chloride (8%, Weight/Aqueous phase final volume=100 mL) and metaphosphoric acid (1%, Weight/Aqueous phase final volume). 4 successive extractions are performed, the residual traces of water are dried by adding several mg of anhydrous sodium sulfate to the organic phase. Following filtration on fiberglass, the organic phase is evaporated until dry in a rotary evaporator and the residue is taken up by 8 mL of HPLC-quality methanol. It is filtered on a 0.45 µm PTFE membrane. The 3,5-diCQ is separated by 15 successive chromatographies on a WATERS® 600 semipreparative HPLC chain (solvents: ultrapure water acidified to 2.6 pH by o-phosphoric acid (solvent A) and HPLC methanol (solvent B)) on an INTERCHIM column (length 250 mm; diameter 21.2 mm) filled with a 10 µm C18 Uptisphere stationary phase and brought to 30° C. The system's flow rate is 18 mL/min. The injected volume is 500 µL. The gradient used is as follows: 0 min.: 35% B; 10 min.: 35% B; 23 min.: 38% B; 33 min.: 38% B. The 3,5-diCQ is collected in the mobile phase approximately 25 min. following the injection. The collected fractions are reduced via concentration using a rotary evaporator until an aqueous phase of approximately 70 mL is obtained. It is brought up to 100 mL with distilled water and it is extracted 3 times with 200 mL of ethyl acetate after adding sodium chloride (10% Weight/Aqueous phase final volume=200 mL). The organic phase is dried by adding several mg of anhydrous sodium sulfate. Following filtration on fiberglass, the ethyl acetate is evaporated until dry, then the residue is taken up in 10 mL of methanol. It is filtered on 0.45 µm PTFE membrane. 30 mL of cold ultrapure water is added in order to precipitate the molecule; it is frozen in liquid nitrogen and freeze-dried.

Figure 1:
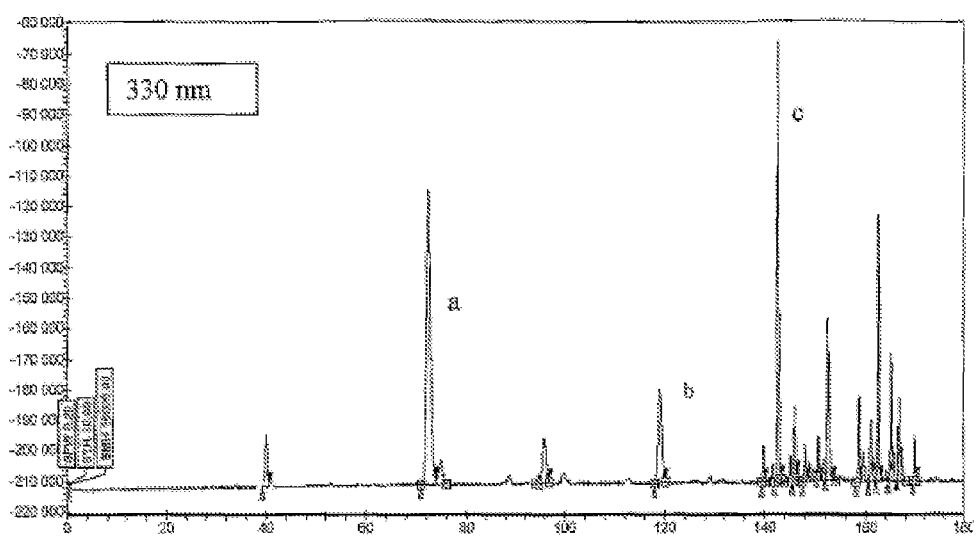
Figures 2, 2A:
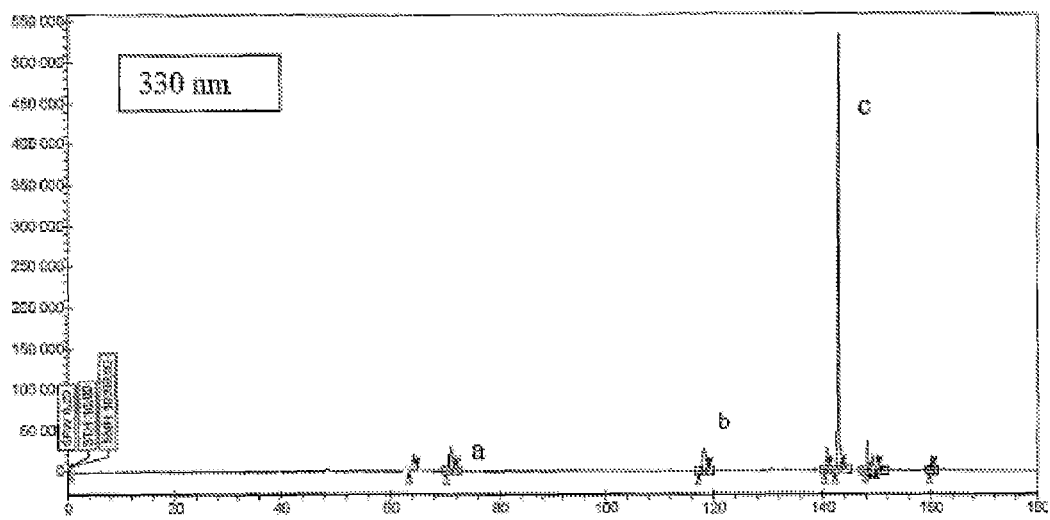
Figure 2B:
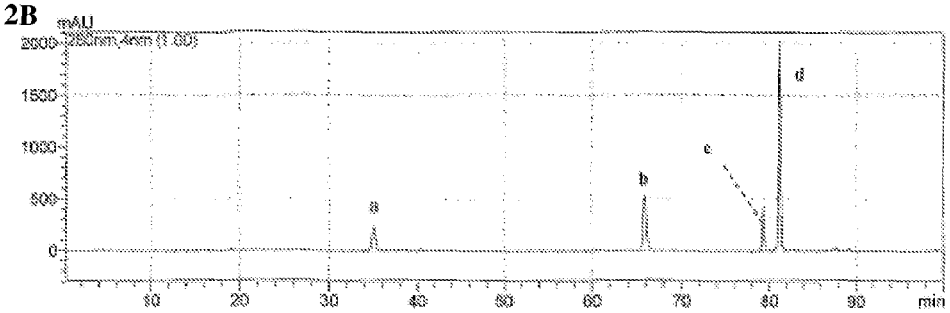
Figure 2C:
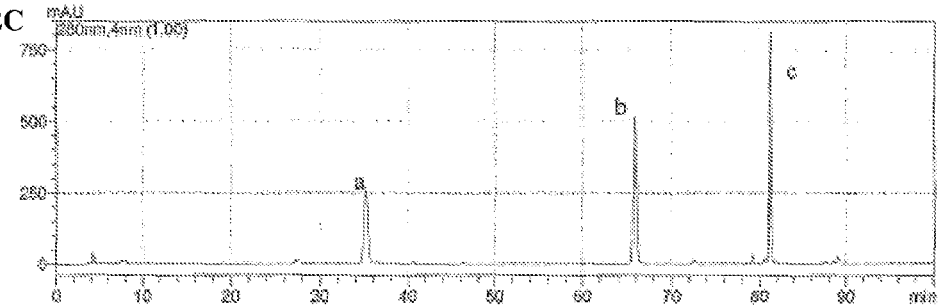
Figure 2D:
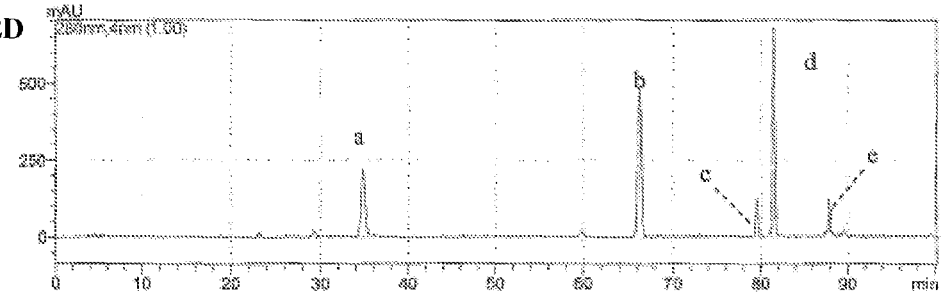
Figure 2E:
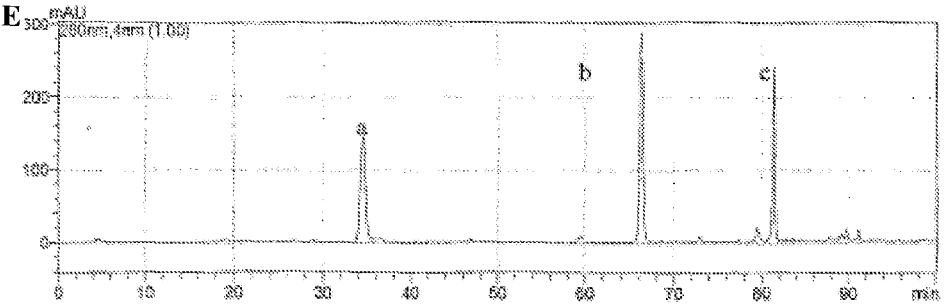
Figure 3:
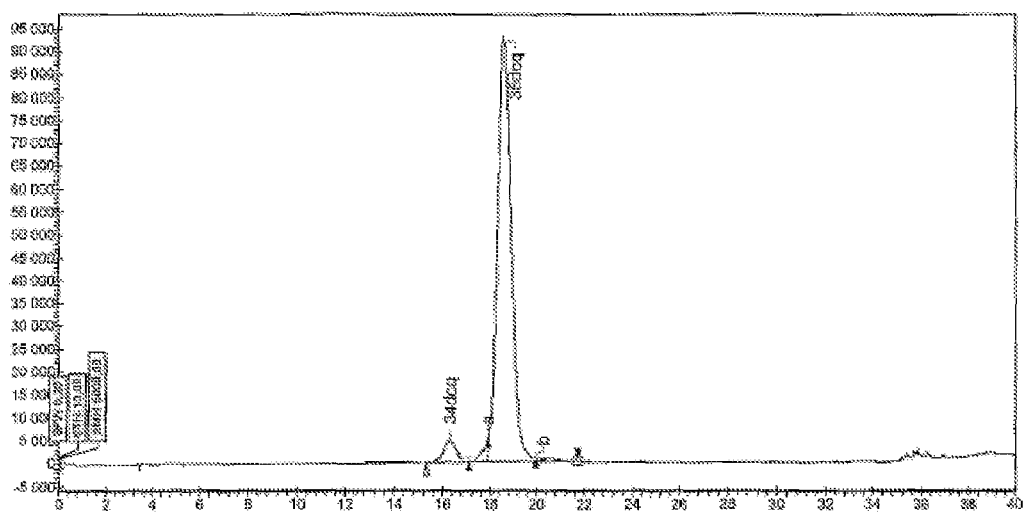
Figure 5:
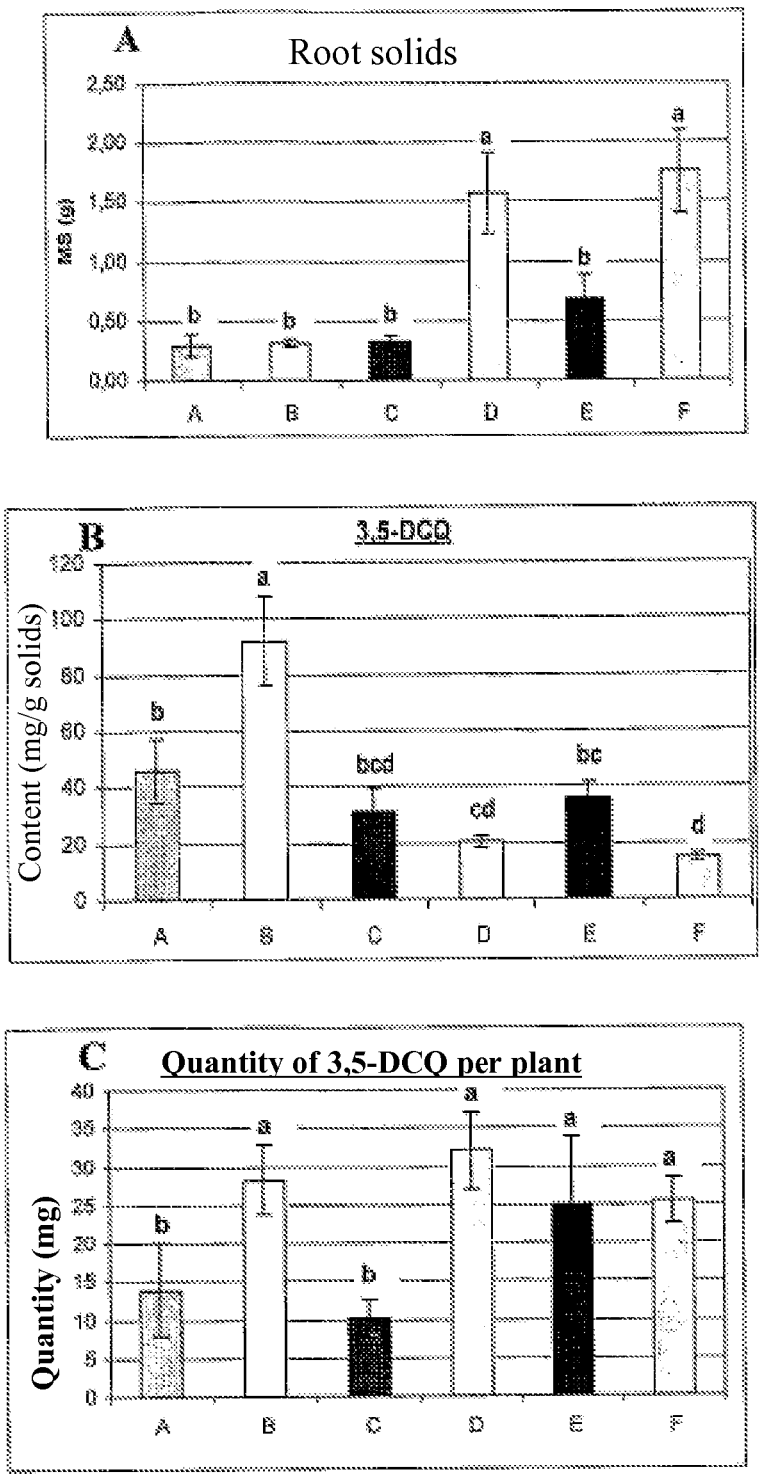
Figure 7:
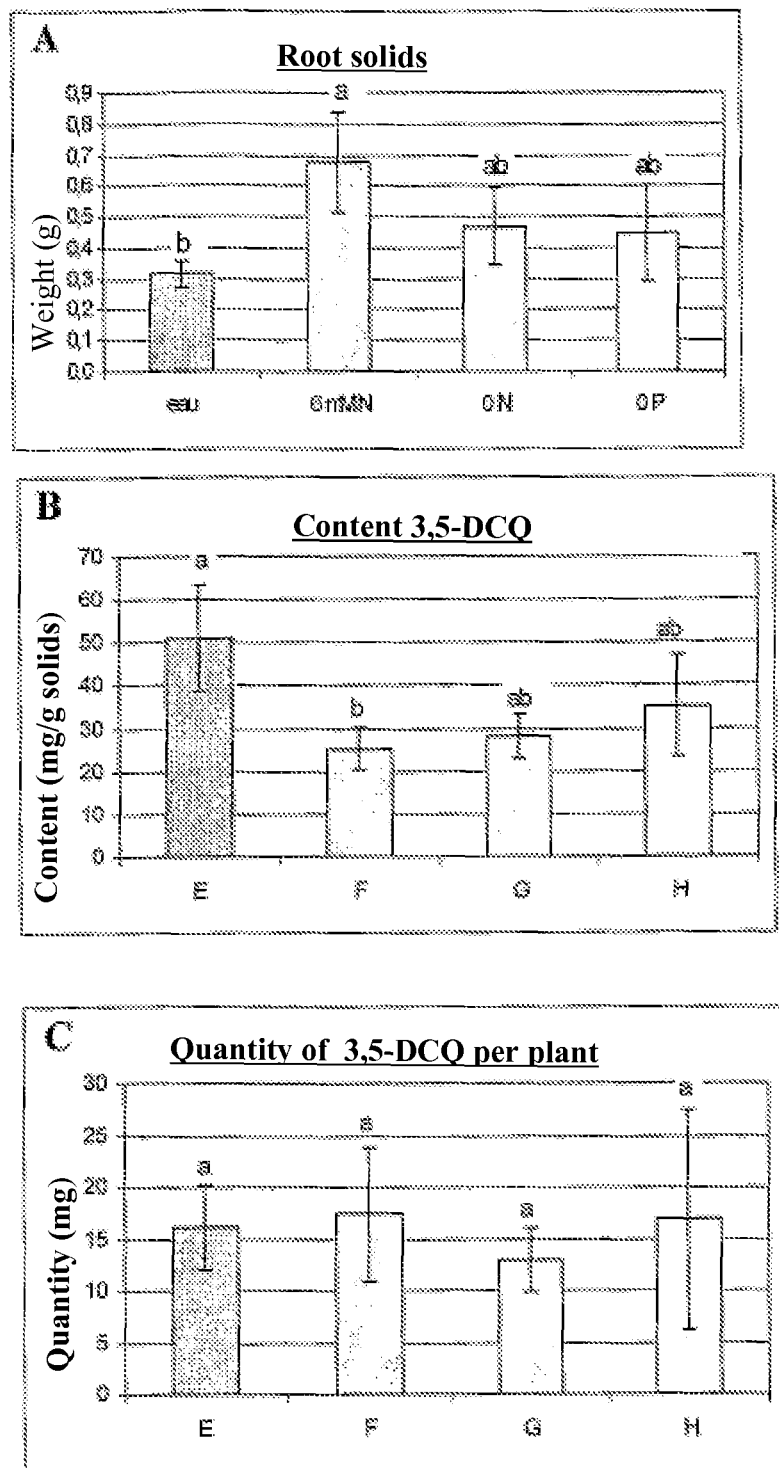

91.9 mg of anhydrous white powder containing approximately 93% 3,5-diCQ and 7% isomeric forms is obtained (FIG. 3, purity control chromatogram of the substance obtained on analytic HPLC chain).

EXAMPLE 2

Favorable Growing Conditions for Producing Dicaffeoylquinic Acids in *Ipomoea batatas* Roots 2.1. Material and Method Two successive experiments (A and B) were performed on a red-fleshed sweet potato variety originally from Guadeloupe (IbD clone) cultivated in 7-L containers in a greenhouse isolated from insects, in Avignon. Cuttings 40 to 50 cm long, composed of the ends of growing stems, were sampled, their basal sections were stripped of leaves in order to prevent the leaves from touching the growing medium, and placed inside transparent plastic receptacles able to hold approximately 1.25 L, filled with the various tested growing media and substrates, and protected (or not protected) from light by an aluminum sheet. The receptacles containing a solid substrate are pierced at the base in order to enable the supplied medium to drain. Since the roots develop at the stem nodes, an equal number of nodes from the base of the cutting were placed inside the growing medium.

Experiment A tested the influence of three different factors on root production and their 3,5-diCQ content: the nature of the growing substrate, aerated or otherwise (perlite or liquid medium), the effect of light (roots grown in darkness or under light), and the influence of the growing medium's mineral composition (complete medium, nitrogen-deficient medium, or distilled water). The various growing conditions compared in Experiment A are illustrated in Table I.

TABLE I

| Condition | Growing medium | Supplied nutrients | Supplied nitrogen | Root lighting |
|---|---|---|---|---|
| A | Liquid | Distilled water | 0 mM | Darkness |
| B | Liquid | Distilled water | 0 mM | Light |
| C | Liquid | Feeding solution | 0.05 mM | Darkness |
| D | Liquid | Feeding solution | 6 mM | Darkness |
| E | Perlite | Distilled water | 0 mM | Darkness |
| F | Perlite | Feeding solution | 6 mM | Darkness |

Experiment B compared the influence of total nitrogen and phosphate deficiencies on root production and their 3,5-diCQ content. The various growing conditions compared in Experiment B are illustrated in Table II.

TABLE II

| Condition | Growing medium | Supplied nutrients | Supplied nitrogen | Supplied phosphorus | Root lighting |
|---|---|---|---|---|---|
| E | Liquid | Distilled water | 0 mM | 0 mM | Darkness |
| F | Liquid | Feeding solution | 6 mM | 1 mM | Darkness |
| G | Liquid | Feeding solution | 0 mM | 1 mM | Darkness |
| H | Liquid | Feeding solution | 6 mM | 0 mM | Darkness |

5 and 3 repetitions per condition were respectively instituted for experiments A and B. The plants, placed in randomized fashion, were grown in a climate-controlled enclosure at a temperature of 25° C. and under a photoperiod of 16 hours of daylight and 8 hours of night. The volume of the liquid medium was regularly topped up to the initial level and the plants cultivated on a solid substrate were frequently watered with the growing solution. The formed roots were sampled after growing for four weeks (Experiment A) or three weeks (Experiment B), weighed, placed in liquid nitrogen, freeze-dried, ground in liquid nitrogen, then freeze-dried again. The obtained powders were analyzed by HPLC for their content of phenolic compounds after extracting them in the ethanol/water solvent (70/30, v/v), evaporating until dry, taking up the dry extract in methanol, and filtering.

In both experiments, the supplied feeding solution is a complete feeding solution including macro- and micro-elements whose composition is provided in Table III. The nitrogen content, supplied exclusively in nitrate form, and the phosphate content vary depending upon the deficiency situations being studied.

TABLE III

| In mg (or μL) per L | Solutions | | | |
|---|---|---|---|---|
| Product | 6 mM N* | 0.05 mM N | 0 N | 0 P |
| $K_2SO_4$ | 174 | 174 | 174 | 261 |
| $Ca(NO_3)_2, 4H_2O$ | 708 | 6 | 0 | 708 |
| $MgSO_4, 7H_2O$ | 370 | 370 | 370 | 370 |
| $CaSO_4, 2H_2O$ | 86 | 598 | 603 | 86 |
| EDTA—Fe, $1H_2O$ | 17 | 17 | 17 | 17 |
| $KH_2PO_4$ | 136 | 136 | 136 | 0 |
| Kanieltra 6 Fe (μL) | 100 | 100 | 100 | 100 |

2.2 Results

These are provided in FIGS. 4 through 7.

The results from Experiment A (FIGS. 4 and 5) show that growing conditions strongly influence 3,5-diCQ content in the roots.

Maximum 3,5-diCQ contents are observed in roots produced in distilled water and under light (Condition B), where they exceed 9% of solids. Contents are minimal in roots produced on a Perlite-type aerated substrate with a complete mineral solution (Condition F). However, they remain high, with 1.5% of solids, under these growing conditions comprising a mineral solution containing nitrogen solely in nitrate form. The contents obtained in the other growing conditions show that root production in a liquid medium and in a nitrogen-deficient situation tends to increase 3,5-diCQ content (FIGS. 4 and 5B).

The quantity of roots produced from cuttings is also greatly affected by growing conditions. The quantity of root solids under complete fertilization conditions (conditions D and F) is much higher than that produced under the other conditions (FIGS. 4 and 5a). This results in an equivalent total quantity of 3,5-diCQ produced per cutting under the conditions that enable high 3,5-diCQ content in the roots but that penalize their growth (Condition A) and under the conditions that yield a lower 3,5-diCQ content but that enable strong root growth (conditions D and F) (FIGS. 4 and 5C).

The results from Experiment B (FIGS. 6 and 7) show that mineral deficiency conditions, involving nitrogen or phosphate, influence 3,5-diCQ content in the roots.

As in Experiment A, the highest 3,5-diCQ contents are obtained when grown in distilled water and the lowest are obtained in the complete mineral solution. When grown in nitrogen- or phosphate-deficient mineral solutions, 3,5-diCQ contents are intermediary (FIGS. 6 and 7B). This shows that phosphate and nitrogen deficiency conditions both tend to increase 3,5-diCQ content in the roots as compared to the complete fertilization conditions, but less so than the situation involving total deficiency of mineral elements, in distilled water. Conversely, these nitrogen and phosphate deficiency conditions limit root growth as compared to the complete mineral solution; less so, however, than in distilled water (FIGS. 6 and 7a). As a result, the quantity of 3,5-diCQ produced in the roots per cutting is equivalent for all conditions (FIGS. 6 and 7C).

2.3. Conclusion

Growing conditions strongly influence the 3,5-diCQ content of nontuberized roots from the *Ipomoea batatas* sweet potato. Growing in a liquid medium, under light, and in a mineral deficiency situation, specifically one deficient in nitrogen and phosphate, are factors that encourage the accumulation of 3,5-dicaffeoylquinic acid in the roots produced by cuttings. The highest content levels, greater than 90 $mg.g^{-1}$ of solids, were obtained in roots produced in water and under light. However, these growing conditions considerably limit the production of roots obtained by stem cutting. Growing cuttings in a complete feeding solution containing nitrogen solely in nitrate form enables greater root production and offers a relatively high 3,5-diCQ content, varying from 20 to 25 $mg.g^{-1}$ of solids.

EXAMPLE 3

Development of a Root Production System Involving Layering 3.1. Material and Methods Samples of stems with growing tips, approximately 110 cm long, were taken on the sweet potato IbD clone. Leaves were removed from their base over four nodes, over a length of approximately 20 cm, and the base was propagated in a climate-controlled room in receptacles able to hold approximately 1.25 L, which contained distilled water or a complete mineral solution and were protected from light by an aluminum sheet. The compositions of the feeding solutions used for the propagation by cutting of *Ipomoea batatas* roots are shown in Table III. The plants were cultivated in a climate-controlled enclosure at a temperature of 25° C. and under a photoperiod of 16 hours of daylight and 8 hours of night. The volume of the liquid medium was regularly topped up to the initial level. After growing for 15 days, the plants are rooted and act as stock for layer production. To do this, on each plant, a stem portion having about ten nodes was defoliated and propagated by layering via immersion in tanks holding approximately 20 L, which were filled with water or mineral solution and protected from light by an aluminum sheet.

Four experiment conditions were instituted that varied the cutting or layering medium, using water or complete mineral solution. These experiment conditions are illustrated in Table IV.

TABLE IV

| Condition | Cutting medium (grown for 4 weeks) | Layering medium (grown for 2 weeks) |
|---|---|---|
| A | Distilled water | Distilled water |
| B | Distilled water | Feeding medium 6 mM nitrogen |
| C | Feeding medium 6 mM nitrogen | Feeding medium 6 mM nitrogen |
| D | Feeding medium 6 mM nitrogen | Distilled water |

3 plants were grown per condition. The roots were sampled on the cut section and on the layered section of each plant 15 days after the stems were propagated by layering, or 4 weeks after propagation by cutting was instituted.

The formed roots were sampled, weighed, placed in liquid nitrogen, freeze-dried, ground inside the liquid nitrogen, then freeze-dried again. The obtained powders were analyzed via HPLC for their content of phenolic compounds after they were extracted in the ethanol/water solvent (70/30, v/v), evaporated until dry, the dry extract was taken up in methanol, and filtered.

3.2. Results

Figure 9:
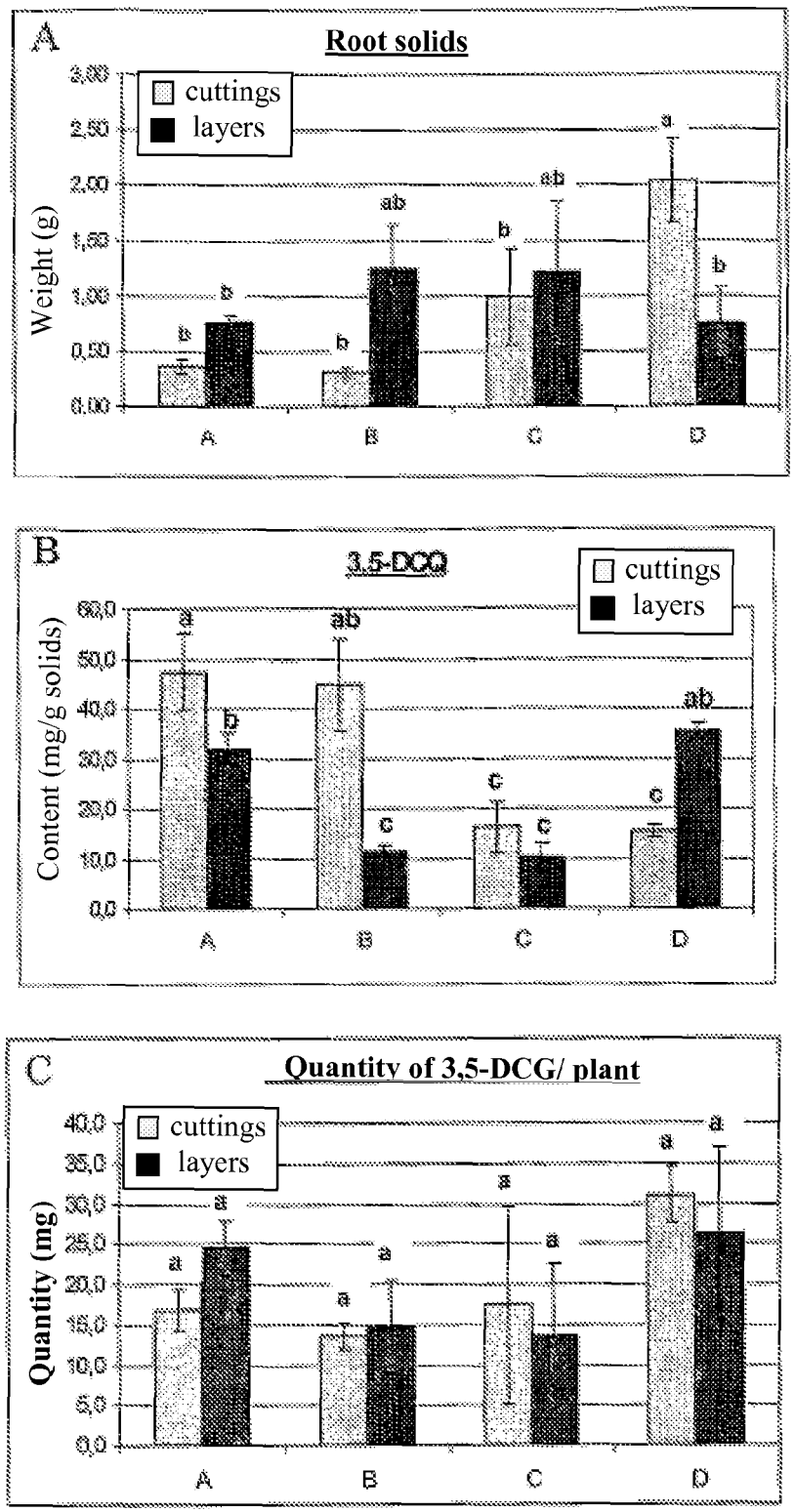

These are provided in FIGS. 8 and 9.

The results clearly show that the 3,5-diCQ content depends upon the growing medium used locally for root production, regardless of whether it involves cutting or layering, and is not influenced by the nature of the medium supplied for the production of the distant root system (FIGS. 8 and 9B).

Average 3,5-diCQ content levels in the roots produced in water vary from 44.7 to 47.4 mg.$g^{-1}$ of solids in the roots from cuttings and from 31.9 to 35.5 mg.$g^{-1}$ of solids in the roots from layers. Average 3,5-diCQ content levels in the roots produced in the mineral solution are three times lower. They vary from 15.5 to 16.2 mg.$g^{-1}$ of solids in the roots from cuttings and from 10.2 to 11.6 mg.$g^{-1}$ of solids in the roots from layers.

The nature of the locally-supplied medium influences the quantity of produced solids (FIG. 8A). Unexpectedly, however, it also appears to be influenced by the growing medium used for producing the distant growing medium. Indeed, the average quantity of roots originating from cuttings produced in the mineral solution (Condition D) is significantly greater when the layers are made in water than that of the cuttings whose layered section is in the mineral solution (Condition C). The total average quantities of 3,5-diCQ produced in the roots formed by cutting (31.1 mg.$g^{-1}$ of solids), by layering (26.2 mg.$g^{-1}$ of solids), and the sum of the latter two figures (57.3 mg.$g^{-1}$ of solids) are highest in this Condition D (cutting in the mineral solution and layering in water).

3.3. Conclusion

The 3,5-diCQ content in the roots obtained by layering depends upon the growing medium used locally for their production and is not influenced by the growing conditions of the stock. The layering in water of normally-fertilized sweet potato plants enables the production of roots with high 3,5-diCQ content levels. This system reconciles considerable growth by the stock through appropriate mineral supply with the production of roots originating from layering that have high 3,5-diCQ content levels. The relevance of this system was validated in an outdoors growth setting on two sweet potato clones, cultivated in a greenhouse container and fertilized normally. The stems layered in water produced, in 15 days, a considerable root mass with high 3,5-diCQ levels (IbD Clone: 32.7 mg.$g^{-1}$ of solids; IbE Clone: 40.4 mg.$g^{-1}$ of solids).

EXAMPLE 4

Measurement of the Repulsivity of 3,5-diCQ, its Isomers, and Mixtures Thereof in Relation to the Green Peach Aphid (*Myzus Persicae*)

4.1. Procedure

The method used is the one developed by Yvan Rahbé (Rahbé & Febvay (1993) Entomologia Experimentalis et Applicata 67: 149-160; Chen (1996) Thesis, Institut National des Sciences Appliquées, Lyon, France: 158 pp.) in the context of research on the chemical determinants of plant resistance to various aphid species (*Aphis gossypii, Acyrthosiphon pisum*), and adapted to the green peach aphid, *Myzus persicae*.

Figure 11:
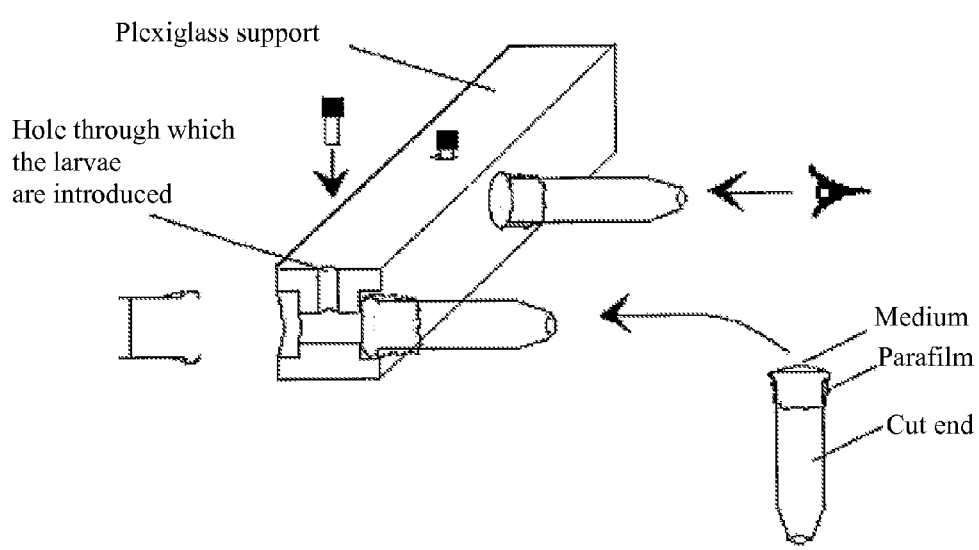

The goal is to evaluate the attractive or repulsive character of a candidate molecule, at various concentrations, either in relation to a control base medium or in relation to another substance. The base medium used, referred to as Ap3 (composition in the table in FIG. 10), was developed at the UMR INRA-INSA in Lyon in order to enable optimal development of the *Acyrtosiphon pisum* aphid species (Febvay et al. (1988) Canadian Journal of Zoology 66: 2149-2453). It also enables the development of *Myzus persicae*. This base medium may or may not be supplemented by the various phenolic acids tested. The aphid's selected behavior when placed in the presence of both media is studied inside a closed system where the insect has no alternative in order to feed itself but to select one of the two media. The device is shown in diagram form in FIG. 11.

The medium (35 μl) is poured between two Parafilm® membranes stretched onto an Eppendorf® cone. On a rack holding 6 experiment cages, a control medium is arranged opposite a test medium on each cage. The repetitions of a single modality (control medium or test medium) are arranged in alternating fashion along the rack, in order to prevent any systematic bias when the aphids are placed inside. At the end of the day, six aphid larvae (second or third stage) are placed inside each of the cages of one rack. Next, the racks are inserted into a black box placed inside a climate-controlled test chamber at 19° C. for 15 hours. This passage into darkness stabilizes the larvae's fixation more quickly. The following morning, the number of aphids fixed on each medium is recorded. The tests are performed in routine fashion on 24 selection repetitions (4 racks with 6 cages each). A phagostimulation index, representing the degree of desire for the aphid in the test medium, is calculated as follows:

Phagostimulation index=(Test no.−Control no.)/Total no., wherein:

Test no.=Number of aphids fixed on the test medium,
Control no.=Number of aphids fixed on the control medium,
Total no.=Total number of fixed aphids.

Consequently, the value of the index ranges from −1 to 1. A negative index means that the test medium is repulsive in relation to the control medium, and a positive index means that the test medium is attractive. The hypothesis that the effect of the test medium is identical to that of the control medium is examined by the Wilcoxon rank test.

The tested phenolic substances other than 3,5-diCQ are of commercial origin apart from the caffeic acid methyl ester, which was synthesized. The molecules were characterized by mass spectrometry and proton nuclear magnetic resonance. The amount and stability of the dissolved molecules are monitored by HPLC after the molecules are dissolved in the Ap3 medium, at the beginning and at the end of the experiment.

4.2. Results 4.2.1 Repulsive Effect of 3,5-diCQ

Figure 12:
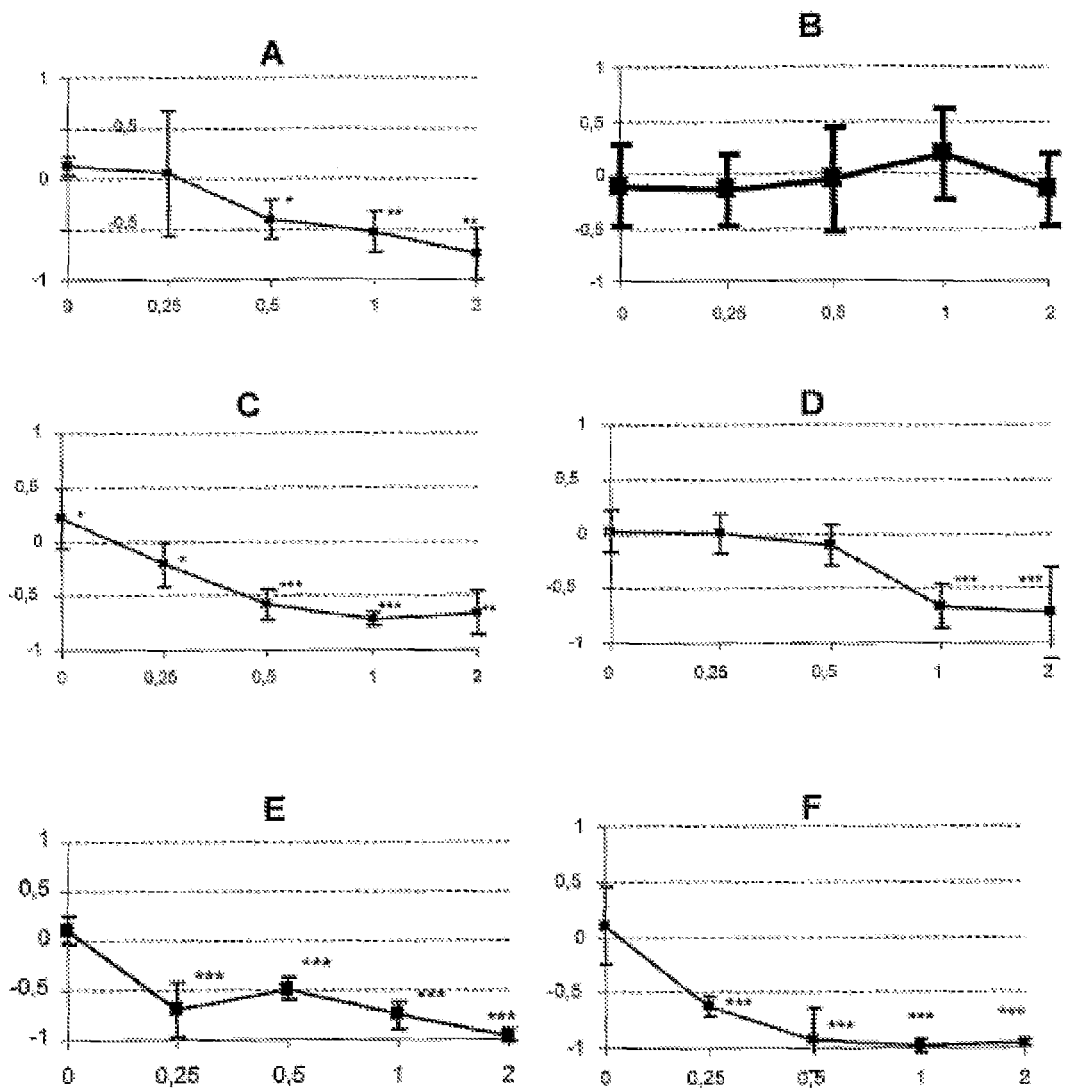
Figure 13:
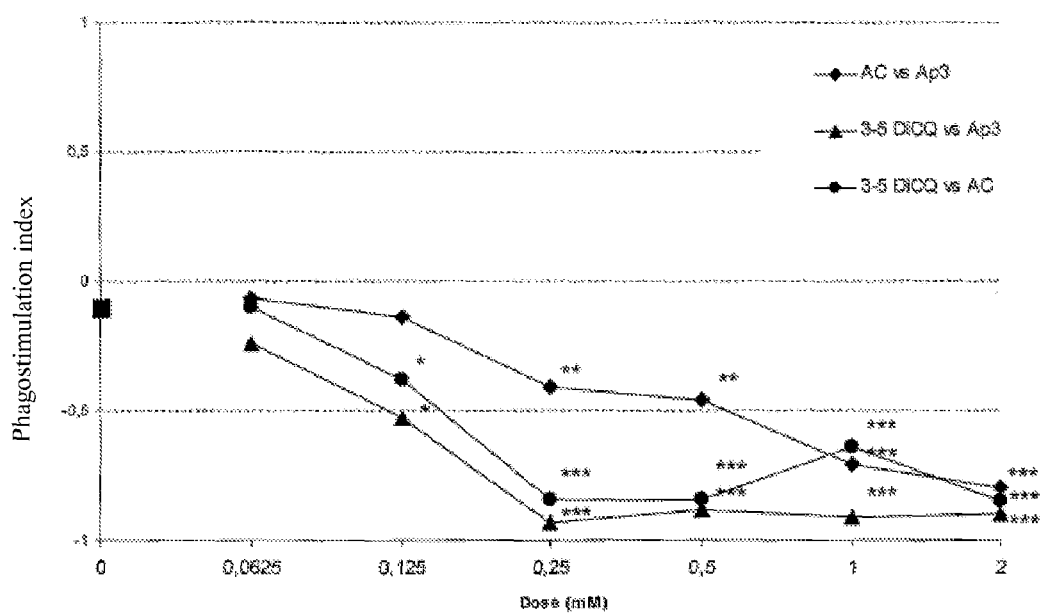
Figure 14:
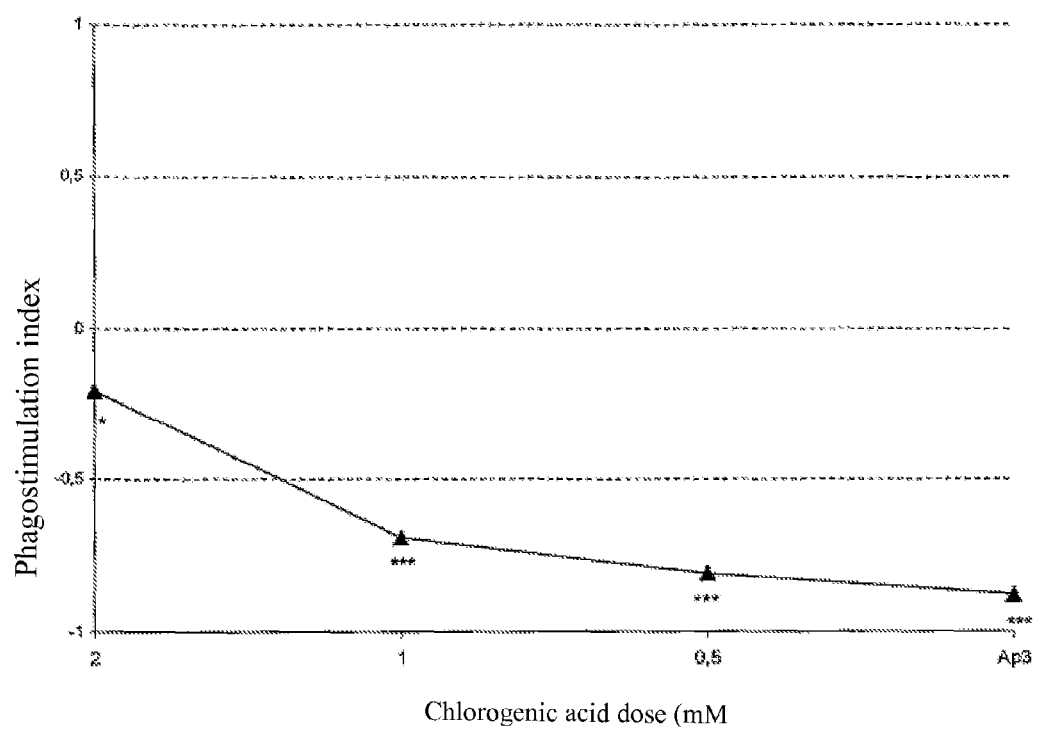

These are provided in FIGS. 12 through 14.

The results obtained show a significant repulsive effect from all of the caffeic derivatives.

3,5-diCQ and caffeic acid methyl ester are the two most repulsive compounds: they have a highly significant effect even at the lowest concentration (0.25 mM), whereas the effects of chlorogenic acid and of cynarin are only significant at concentrations of 0.5 mM and 1 mM, respectively. Paracoumaric acid, which is a monohydroxylated phenolic molecule, has no repulsive effect on *Myzus persicae* in the concentration range tested (FIG. 12). We also verified that a control solution made with the solvents and additives used for extracting and purifying 3,5-diCQ only shows a repulsive effect at a concentration that is much higher than that used when preparing the molecule (data not shown).

3,5-diCQ is significantly repulsive at the concentration of 0.125 mM and chlorogenic acid (CA) at 0.25 mM (FIG. 13). For a single molarity, the aphid systematically selects CA rather than 3,5-diCQ at 0.125 mM. We obtained identical results by using an Ap3 medium at 5.3 pH wherein the tested substances showed no browning, contrary to the original Ap3 medium set at 7.5 pH, wherein the caffeic substances show major browning (results not shown).

When we vary the CA concentration from 0.5 mM to 2 mM with 0.5 mM of 3,5-diCQ, the obtained results show that the 3,5-diCQ at a molarity of 0.5 mM remains repulsive in relation to chlorogenic acid at a concentration that is four times higher (2 mM) for a pH of 7.5 (FIG. 14). Similar results were obtained at 5.3 pH.

All of the results obtained show a clear repulsive effect of 3,5-dicaffeoylquinic acid in relation to the green peach aphid (*Myzus persicae*). This effect is detectable at a minimum concentration of 125 μM (or 64.5 mg.L$^{-1}$). The repulsive effect of this molecule is clearly greater than that of its metabolic precursor, chlorogenic acid.

4.2.2 Repulsive Effect of 3,5-diCQ Isomers and of Mixtures Thereof on *Myzus persicae*

Figure 15:
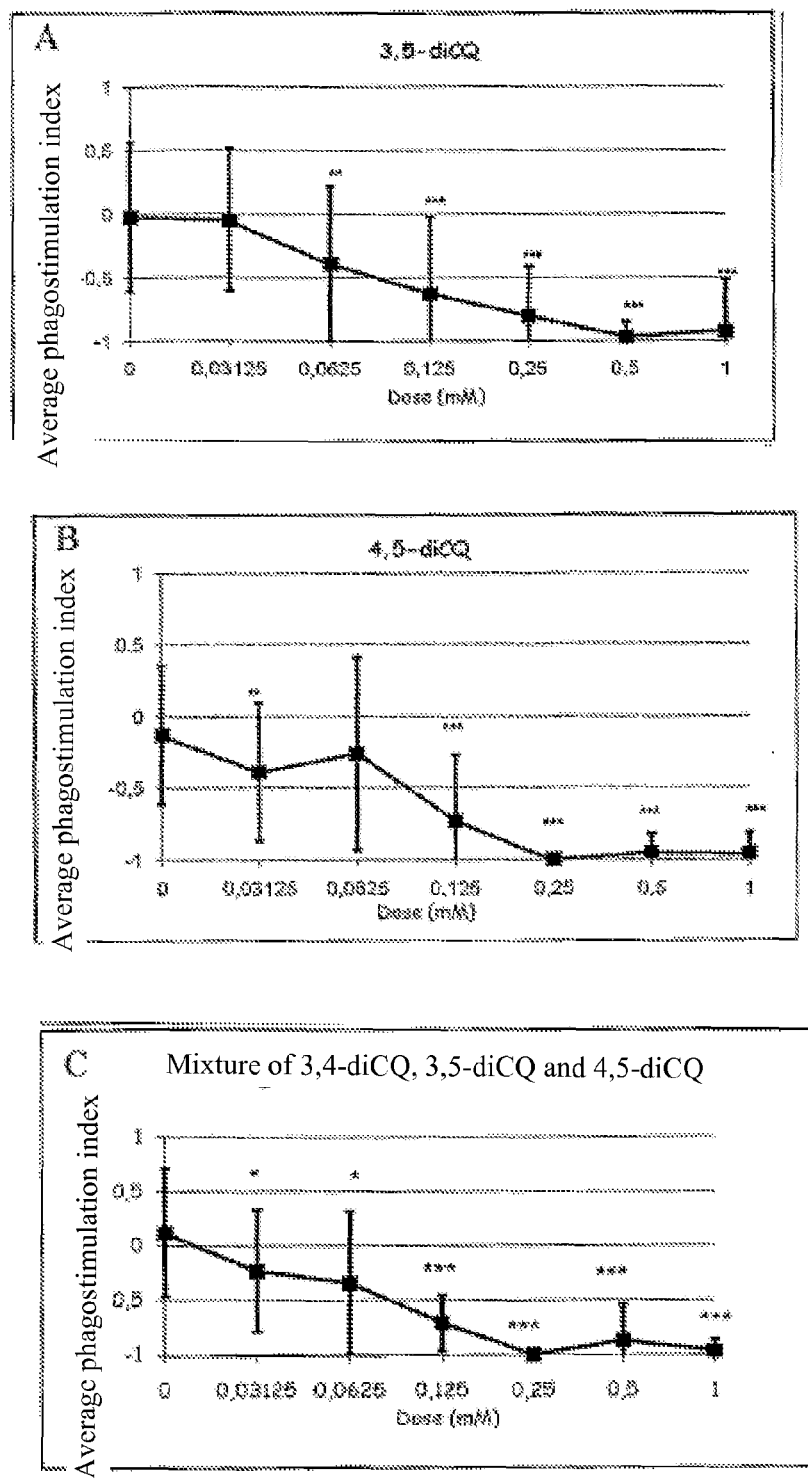
Figure 16A:
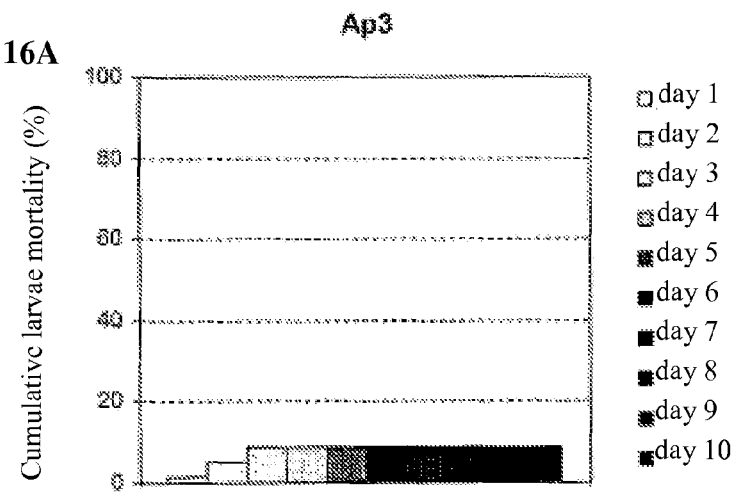
FIG. 16A, FIG. 16B, FIG. 16C and FIG. 16D illustrate the cumulative larval mortality of *Myzus persicae* obtained during tests for evaluating the toxicity of 3,5-dicaffeoylquinic (3,5-diCQ) acid, of its precursor chlorogenic acid (CA), of the Ap3 control medium, and of the control extract obtained from solvents and additives used for purifying 3,5-diCQ. The Ap3 medium is adjusted to 7.5 pH.
Figure 16B:
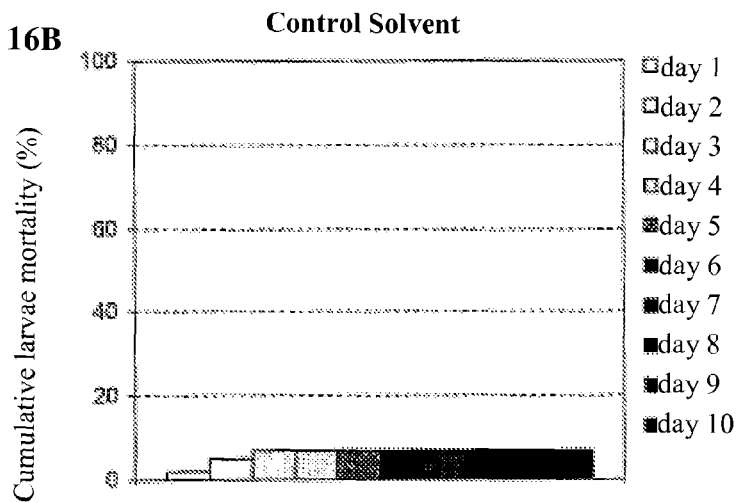
Figure 16C:
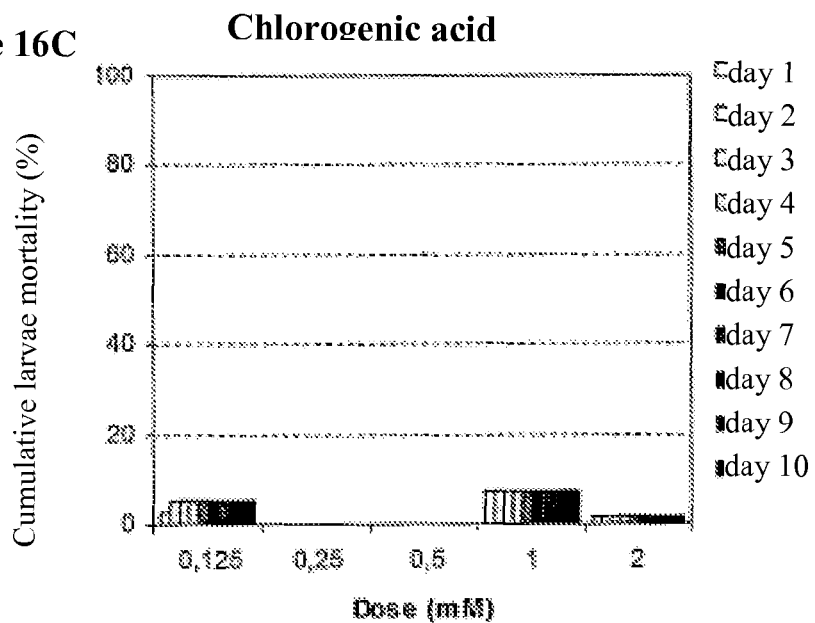
Figure 16D:
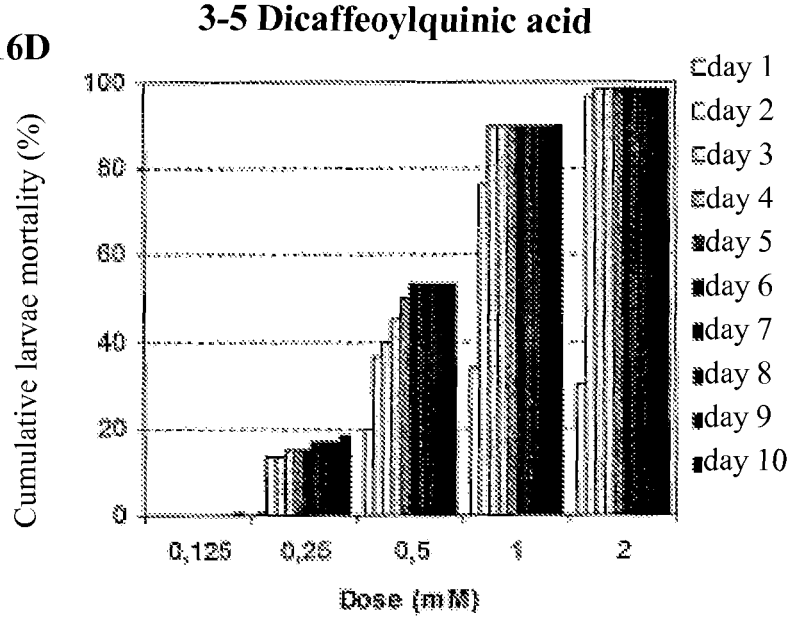

The results are given in FIG. 15.

The repulsive effects of 3,5-diCQ, of 4,5-diCQ, and of the 3,4-diCQ/3,5-diCQ/4,5-diCQ mixture (in equal proportions) were tested at the same concentrations. The concentration range of the tested substance varies from 0.03125 to 1 mM.

3,5-diCQ and all of its isomers have a significant repulsive effect. 3,5-diCQ, 4,5-diCQ, and the 3,4-diCQ/3,5-diCQ/4,5-diCQ mixture have a highly significant repulsive effect at the 0.125 mM dose. Significant repulsive effects were detected starting at the 0.03125 mM dose for 4,5-diCQ and the 3,4-diCQ/3,5-diCQ/4,5-diCQ mixture.

3,5-dicaffeoylquinic acid, 4,5-dicaffeoylquinic acid, and the 3,4-diCQ/3,5-diCQ/4,5-diCQ mixture all offer repulsive activity on *Myzus persicae*. This activity varies depending upon the molecule presented to the aphid. This suggests that the acylation position of caffeic acids on quinic acid influences the repulsive character of dicaffeoylquinic acids.

EXAMPLE 5

Measuring the Toxicity of 3,5-diCQ, its Isomers, and Mixtures Thereof on Larval Development of the Green Peach Aphid (*Myzus persicae*)

5.1 Procedure

The goal is to quantify the toxic effect of 3,5-diCQ on the aphid throughout its larval development, namely 8 to 10 days for *Myzus persicae* at 19° C. The molecule is added at various concentrations to the Ap3 feeding medium.

The medium (75 μA) is poured between two UV-sterilized Parafilm® membranes and drawn onto a cylindrical support made of PVC (h=1.5 cm, d=2 cm), under sterile conditions. On Day D0, 20 neonate larvae are placed inside the cylinder, which is then turned over and pressed onto a square of Parafilm®. The dishes are placed under dimmed light (16 hr day/8 hr night) and in an enclosure set at 19° C. The fixation percentage is recorded after 1 hour as a short-term phagostimulation indicator and in order to verify that no anomaly had occurred when the aphids were placed inside the cylinder. Larval mortality is noted daily at the end of the day. On Day D+3, the larvae are sampled and split up into two new dishes. On the day of their adult molt, the aphids that have reached the wingless adult stage are deposited successively onto a precision scale (d=0.01 mg) and the cumulative weights are recorded for each concentration of each tested molecule. Individual weights are calculated thereafter. The effects of a single molecule at all concentrations and the effects of the control medium are evaluated simultaneously during the same test. The tests are routinely performed in 3 repetitions.

5.2. Results 5.2.1. Toxic Effect of 3,5-diCQ on *Myzus persicae*

5.2.1.1. Effect on Larval Mortality

The results are given in FIG. 16.

We observe a very marked effect of 3,5-diCQ on aphid larvae mortality, which increases gradually during the insect's development. Mortality also increases with concentration, reaching nearly 100% at 2 mM. Conversely, mortality never exceeds 10% on the Ap3 medium, on the control extract obtained from solvents and additives used for purifying 3,5-diCQ, and on chlorogenic acid (including at the highest concentrations).

5.2.1.2. Effect on the Weight of Wingless Adults

Figure 17:
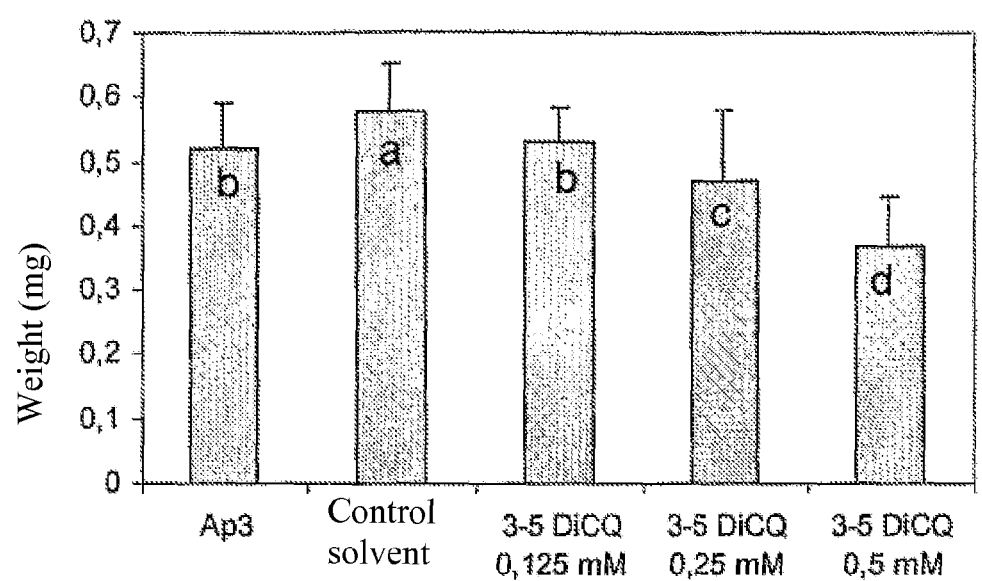
FIG. 17 illustrates the weight of wingless adults (average+1 standard deviation) of *Myzus persicae* raised on Ap3 control medium, on the control extract obtained from solvents and additives used for purifying 3,5-diCQ, and on 3,5-dicaffeoylquinic (3,5-diCQ) acid. The averages followed by the same letter are not significantly different at the 5% threshold (Student-Newman-Keuls test).
Figure 18:
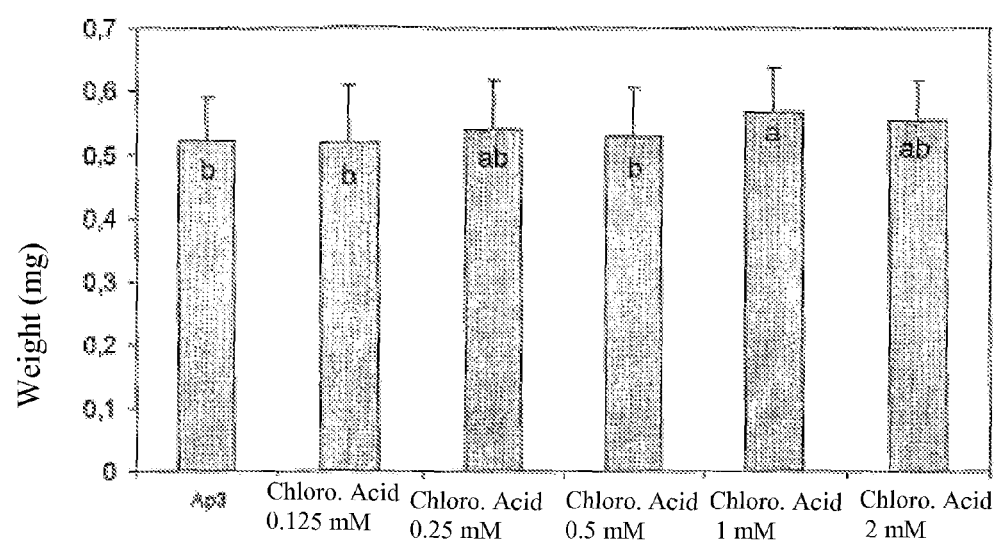
FIG. 18 illustrates the weight of wingless adults (average+1 standard deviation) of *Myzus persicae* raised on Ap3 control medium and on chlorogenic acid. The averages followed by the same letter are not significantly different at the 5% threshold (Student-Newman-Keuls test).

The results are given in FIGS. 17 and 18.

Weighings of surviving wingless adults obtained at the end of their development show a significant depressive effect of 3,5-diCQ starting at the 0.25 mM dose (FIG. 17) (ANOVA: F=32.86, P<0.0001). The 1 and 2 mM concentrations of 3,5-diCQ are not shown because no aphids reached the wingless adult stage on these modalities. This depressive effect on aphid weight is not observed for chlorogenic acid, which appears to have a probiotic effect (FIG. 18; ANOVA: F=3.31, P=0.0063).

In vitro tests show that 3,5-diCQ causes high mortality in larvae during their development and significantly lowers the weight of obtained adults, whereas the metabolic precursor CA shows no negative effects on larval development.

5.2.2. Toxic Effect of 3,5-diCQ Isomers and of Mixtures Thereof on *Myzus persicae*

5.2.2.1. Effects on Larval Mortality

Figure 19:
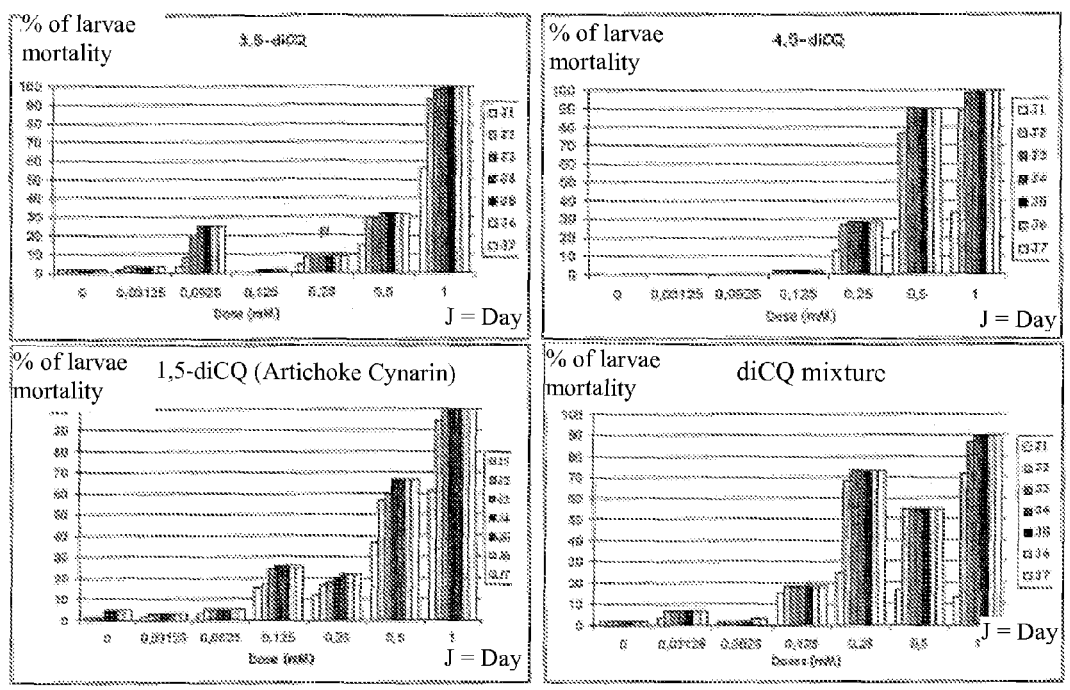
FIG. 19 illustrates the cumulative daily mortality observed during larval development of *Myzus persicae* (7 days) in the presence of 3,5-dicaffeoylquinic acid, of two of its isomers (4,5-diCQ, 1,5-diCQ), and of the 3,4-diCQ/3,5-diCQ/4,5- diCQ mixture. The concentration range of the tested substance varies from 0.03125 mM to 1 mM. Dose 0 corresponds to the Ap3 control medium alone.

The results are given in FIG. 19.

We observe a very marked toxic effect of all of the tested isomers and of the isomer mixture at the 1 mM dose (80 to 100% cumulative mortality observed starting on the $3^{rd}$ day of larval development). 4,5-diCQ and 1,5-diCQ show a clear toxic effect at the 0.5 mM dose (cumulative mortality greater than 50% on the $3^{rd}$ day). The isomer mixture causes cumulative mortality greater than 50% on the $3^{rd}$ day starting at the 0.25 mM dose.

5.2.2.2. Effect on the Weight of Wingless Adults

The results are given in FIG. 20.

Weighings of wingless adults obtained at the end of their development (FIG. 20) show a significant depressive effect at the 0.5 mM dose for 3,5-diCQ (ANOVA: F=10.856, P<0.0001). This depressive effect on the aphids' weight is observed starting at the 0.25 mM dose for 4,5-diCQ (ANOVA: F=38.61, P<0.0001) and the isomer mixture (ANOVA: F=39.248, P<0.0001). Conversely, no effect on the aphids' weights is observed for cynarin at the 0.25 mM dose (ANOVA: F=2.291, P=0.068).

3,5-dicaffeoylquinic acid, 4,5-dicaffeoylquinic acid, 1,5-dicaffeoylquinic acid, and the mixture of 3,4-dicaffeoylquinic/3,5-dicaffeoylquinic/4,5-dicaffeoylquinic acids all have toxic activity on *Myzus persicae*.

EXAMPLE 6

In Vitro Evaluation of the Effect of 3,5-dicaffeoylquinic Acid on Other Aphid Species 6.1. Animal Material and Methods Two aphid species, including the green or pink pea aphid, *Acyrthosiphon pisum*, and the green and pink potato aphid, *Macrosiphum euphorbiae*, are used in this study.

*Acyrthosiphon pisum* (Harris) is a large aphid that colonizes wild-growing and cultivated leguminous plants such as sainfoin, alfalfa, vetch, peas, beans, and clover. The aphid clone provided by the UMR BF2I INRA/INSA in Lyon is raised in a climate-controlled room on beans.

*Macrosiphum euphorbiae* (Thomas) is a large, spindle-shaped aphid. Highly polyphagous and cosmopolitan, it is seen primarily on potatoes, beets, cabbage, greenhouse-raised plants (lettuce, chicory, peppers, eggplants, cucumbers), wild plants, and commercially-grown flowers: cineraria, chrysanthemums, dahlias, carnations, etc. The aphid clone, provided by the Plant Biology and Pest Control Laboratory at the Universite de Picardie Jules Verne in Amiens, was raised in a climate-controlled room on potatoes.

The protocol implemented and the feeding medium was identical to those described earlier for *Myzus persicae* except for the larval stage used. Given the size of these two species, in order to leave sufficient space for the larvae inside the experiment device, first-stage larvae (L1) were used for this type of test.

Regarding the toxicity tests, no changes were made to the protocol for tests on *Macrosiphum euphorbiae*. However, given the size and sensitivity to stress of *Acyrthosiphon pisum*, the number of individuals per dish was changed to 10, the number of repetitions per tested dose was changed to 4, and no change was made to the medium during the test, as excessive disturbance of the aphids would have resulted from doing so.

6.2. Results 6.2.1. Repulsive Effect and Toxicity of 3,5-diCQ on *Acyrtosiphon pisum*

6.2.1.1 Phagorepulsive Effect

The results obtained (FIG. 21) show a significant repulsive effect of 3,5-diCQ starting at the 0.03125 mM dose.

6.2.1.2. Toxic Effect During Larval Development

FIG. 22 shows a very marked effect of 3,5-diCQ on the larval development of *A. pisum* since mortality exceeds 50% starting at 0.03125 mM within 2 days and reaches 100% starting at 0.25 mM within 4 days. However, it never exceeds 20% on Ap3. This higher mortality rate on the control medium as compared to that observed for *Myzus persicae* is explained by the losses Caused by handling this very fragile aphid.

These results suggest that the minimal dose for detecting repulsive and toxic effects on this aphid species could be lower than 0.03125 mM, at which dose no toxic or repulsive effect is observed in *M. persicae*.

6.2.2 Repulsive Effect and Toxicity of 3,5-diCQ on *Macrosiphum euphorbiae*

6.2.2.1. Phagorepulsive Effect

The obtained results (FIG. 23) show a highly significant repulsive effect of 3,5-diCQ on *M. euphorbiae* starting at the 0.125 mM dose.

6.2.2.2. Toxic Effect During Larval Development

FIG. 24 shows a very marked effect of 3,5-diCQ on the larval development of *Macrosiphum euphorbiae* since mortality reaches 100% within 3 to 7 days for the 0.5 and 1 mM doses, and nearly 100% within 6 days for the 0.25 mM dose.

The invention claimed is:

1. A method for preparing compounds of Formula (I)

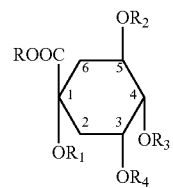

wherein

R represents a hydrogen atom or a methyl group, $R_1$, $R_2$, and $R_4$ each represent, independently of each other, a hydrogen atom or a caffeoyl group, $R_3$ represents a hydrogen, a caffeoyl group, or a succinyl group, provided that at least two of $R_1$ through $R_4$ represent a caffeoyl group, and that $R_3$ represents a succinyl group only if $R_2$ and $R_4$ represent a caffeoyl group, from nontuberized roots of plants of the genus *Ipomoea* comprising the following steps:

a) taking samples of said nontuberized roots or recovering root exudate thereof, b) extraction of phenolic compounds from said roots or said root exudate using one or several organic solvents, and c) recovery of the raw extract.

2. The method according to claim 1 further comprising the step:

d) purification of said extract obtained in Step c).

3. The method according to claim 1 further comprising the step:
   e) spontaneous isomerization of said extracts under alkaline pH conditions; said Formula (I) compounds may be in the form of regio- or stereoisomers, or mixtures thereof.

4. The method according to claim 1, wherein said nontuberized roots originate from plants selected from the group consisting of the sweet potato (*Ipomoea batatas*), morning glory (*Ipomoea purpurea*), water spinach (*Ipomoea aquatica*), oceanblue morning glory (*Ipomoea indica*), and Scarlett O'Hara morning glory (*Ipomoea nil*).

5. The method according to claim 1, wherein said nontuberized roots originate from *Ipomoea batatas*.

6. The method according to claim 1, wherein nontuberized roots are produced by growing in a liquid medium, under light, and under nitrogen deficiency conditions.

7. The method according to claim 1, wherein the Formula (I) compounds are selected from the group consisting of 3,5-dicaffeoylquinic (3,5-diCQ) acid, cynarin (1,3-diCQ), 1,5-dicaffeoylquinic (1,5-diCQ) acid, 3,4-dicaffeoylquinic (3,4-diCQ) acid, 4,5-dicaffeoylquinic (4,5-diCQ) acid, methylated analogues thereof, triacylated analogues thereof and mixtures thereof.

8. The method according to claim 1, wherein the Formula (I) compounds are selected from the group consisting of 3,5-dicaffeoylquinic (3,5-diCQ) acid, cynarin (1,3-diCQ), 1,5-dicaffeoylquinic (1,5-diCQ) acid, 3,4-dicaffeoylquinic (3,4-diCQ) acid, 4,5-dicaffeoylquinic (4,5-diCQ) acid, 3,4,5-tricaffeoylquinic (3,4,5-triCQ) acid, methyl 3,5-dicaffeoylquinate, methyl 3,4-dicaffeoylquinate, methyl 4,5-dicaffeoylquinate, 4-succinyl-3,5-dicaffeoylquinic acid and mixtures thereof.

9. The method according to claim 1 comprising the following steps:
   a) taking samples of said nontuberized roots originating from tubers, cuttings, seedlings, or layers,
   b) freezing said roots sampled in Step a) in liquid nitrogen,
   c) freeze-drying said roots frozen in Step b),
   d) grinding said freeze-dried roots in liquid nitrogen, then lyophilizing the freeze-dried roots in order to obtain a dry powder,
   e) extracting phenolic compounds from the dry powder using an organic solvent in 1 to 4 passes, via cold stirring,
   f) rinsing the final residue from Step e) with the same organic solvent as the one used in Step e), then evaporating the solvent present in the extract until an aqueous phase is obtained,
   g) optionally, liquid/liquid volume-to-volume extraction of the aqueous phase from Step f) using an apolar solvent, via several successive extractions, after adding a salt and an acid to said aqueous phase, to obtain an organic phase;
   h) dry concentration of the aqueous phase obtained in Step f) or of the organic phase obtained in Step g), after adding a drying agent and filtration in order to eliminate residual water, then taking up the dry residue using an organic solvent,
   i) separation the organic phase of Step h) using semi-preparative reversed-phase HPLC and collection of the fraction containing 3,5-diCQ,
   j) concentration of the fraction obtained in Step i) until an aqueous phase is obtained,
   k) liquid/liquid volume-to volume extraction of the aqueous phase obtained in Step j) using an apolar solvent via several successive extractions, after adding a salt to said aqueous phase, in order to facilitate 3,5-diCQ extraction into the apolar solvent, and obtain an organic phase;
   l) dry concentration of the organic phase of Step k), after adding a drying agent and filtration in order to eliminate residual water, and taking up the dry residue using an organic solvent, and
   m) cold precipitation of the compound by adding water in an amount of at least 3 volumes of water for 1 volume of the organic solvent used in the previous step), and freeze-drying of the precipitated compound in order to obtain the compound in the form of a dry powder.

10. The method according to claim 9, wherein Step g) is carried out by extracting with ethyl acetate or diethylether (volume-to-volume) after adding NaCl or ammonium sulfate and metaphosphoric acid into the aqueous phase and Step k) is performed via extraction, either by ethyl acetate or by diethylether (volume to volume) after NaCl or ammonium sulfate is added into the aqueous phase.

11. The method of claim 1, wherein the compounds of Formula (I) are selected from different isomeric forms of dicaffeoylquinic acids, triacylated analogues thereof, methylated analogues thereof, 4-succinyl-3,5-dicaffeoylquinic acid, or mixtures thereof.

12. The method of claim 1, wherein the compounds of Formula (I) are selected from different isomeric forms of 3,5-dicaffeoylquinic (3,5-diCQ) acid, triacylated analogues thereof, methylated analogues thereof or mixtures thereof.

13. The method of claim 1, wherein the compound of Formula (I) is 3,5-dicaffeoylquinic (3,5-diCQ) acid.

14. The method of claim 1, wherein the nontuberized roots are produced by layering, cutting or from seedlings.

15. The method of claim 6 wherein said nontuberized roots originate from plants selected from the group consisting of the sweet potato (*Ipomoea batatas*), morning glory (*Ipomoea purpurea*), water spinach (*Ipomoea aquatica*), oceanblue morning glory (*Ipomoea indica*), and Scarlett O'Hara morning glory (*Ipomoea nil*).

16. The method of claim 6 wherein said nontuberized roots originate from *Ipomoea batatas*.

17. The method of claim 14 wherein said nontuberized roots originate from plants selected from the group consisting of the sweet potato (*Ipomoea batatas*), morning glory (*Ipomoea purpurea*), water spinach (*Ipomoea aquatica*), oceanblue morning glory (*Ipomoea indica*), and Scarlett O'Hara morning glory (*Ipomoea nil*).

18. The method of claim 14 wherein said nontuberized roots originate from *Ipomoea batatas*.

19. The method of claim 9 wherein all of steps a) through m) are performed at a temperature ranging from 3 to 5° C., protected from prolonged light exposure, and the acid pH of the aqueous solvents ranges from 5.0 to 6.0.

* * * * *